(12) United States Patent
Douglas et al.

(10) Patent No.: US 11,570,368 B1
(45) Date of Patent: Jan. 31, 2023

(54) METHOD AND APPARATUS FOR IMAGING ON A DOUBLE CURVED DISPLAY

(71) Applicants: Robert Edwin Douglas, Winter Park, FL (US); Kathleen Mary Douglas, Winter Park, FL (US); David Byron Douglas, Winter Park, FL (US)

(72) Inventors: Robert Edwin Douglas, Winter Park, FL (US); Kathleen Mary Douglas, Winter Park, FL (US); David Byron Douglas, Winter Park, FL (US)

( * ) Notice: Subject to any disclaimer, the term of this patent is extended or adjusted under 35 U.S.C. 154(b) by 0 days.

(21) Appl. No.: 17/832,799

(22) Filed: Jun. 6, 2022

Related U.S. Application Data

(63) Continuation-in-part of application No. 17/561,961, filed on Dec. 26, 2021.

(51) Int. Cl.
| | |
|---|---|
| *H04N 5/232* | (2006.01) |
| *H04N 5/378* | (2011.01) |
| *H04N 5/369* | (2011.01) |
| *H04N 5/225* | (2006.01) |
| *G02B 7/02* | (2021.01) |
| *H04N 13/207* | (2018.01) |

(52) U.S. Cl.
CPC ........... *H04N 5/23296* (2013.01); *G02B 7/02* (2013.01); *H04N 5/2254* (2013.01); *H04N 5/3696* (2013.01); *H04N 5/378* (2013.01); *H04N 5/379* (2018.08); *H04N 13/207* (2018.05)

(58) Field of Classification Search
None
See application file for complete search history.

(56) References Cited

U.S. PATENT DOCUMENTS

| | | | | |
|---|---|---|---|---|
| 5,859,947 | A * | 1/1999 | Kiryuscheva | G02B 7/004 385/136 |
| 5,880,834 | A * | 3/1999 | Chrisp | G01J 3/0294 356/328 |
| 6,345,129 | B1 * | 2/2002 | Aharon | H04N 5/2259 382/284 |
| 2001/0020671 | A1 * | 9/2001 | Ansorge | H01L 27/14603 257/E27.131 |
| 2009/0212219 | A1 * | 8/2009 | Cook | G03B 37/00 359/356 |
| 2017/0102264 | A1 * | 4/2017 | Harder | G01J 1/0422 |
| 2019/0094026 | A1 * | 3/2019 | Jungwirth | G02B 7/005 |
| 2020/0025891 | A1 * | 1/2020 | Sparbert | G02B 26/0875 |

* cited by examiner

*Primary Examiner* — Ross Varndell

(57) ABSTRACT

This patent provides a method and apparatus for acquiring imagery with improve spatial resolution through an apparatus called a "light painting imaging device". Other aspects of this invention correct for barrel distortion and pincushion distortion.

18 Claims, 21 Drawing Sheets

LIGHT PAINTING IMAGING DEVICE (SLPID)

LIGHT PAINTING IMAGING DEVICE

DESIGN FEATURES

- Lens:
  - Positioned on a bi-axial rotatable mount. Preferred embodiment is a fast rotation speed about a first axis and a slow rotation speed about a second axis. Center of rotation is about the center of the lens.
  - Preferred embodiment is a converging lens. Alternative embodiments include a Fresnel lens or a diverging lens.
- Detector array (sensor):
  - Type: CMOS (complementary metal oxide semiconductor) or CCD (charge coupled device)
  - Shape: double curved wherein the center point of the lens is equidistant to all points on the detector array.
  - Other embodiment comprises a stacked layout.
  - Other embodiments include composite construction. Lens options: Fresnel (plastic), Converging (glass)
- Processor
- Memory
- Filters
- Microlenses
- LIDAR / LRF
- Shutter
- Cover for ambient light
- Timing: Data from only a single detector element is recorded at a time epoch
- Calibration with light sources
- Registration of imagery with GPS or reference points (e.g., North Star)
- Multiple units:
  - Cluster of units from a single viewing perspective
  - First imaging set at a first location; second imaging set at a second imaging location for stereoscopic
- Display: Flat Monitor; Extended Reality head display unit; double curved display per US 17/561,961, A method and apparatus of presenting 2D images on a double curved, non-planar display, which is incorporated by reference in its entirety

LIGHT PAINTING IMAGING DEVICE

LENS USED FOR THE LIGHT PAINTING IMAGING DEVICE
Fig. 3A Rapid scanning lens coordinate system
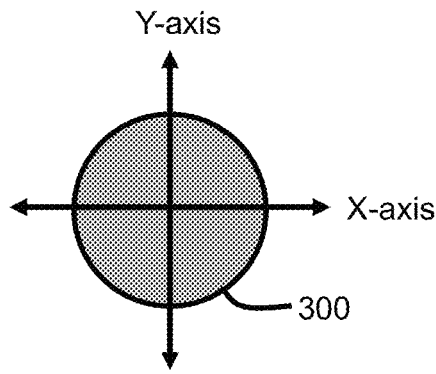
Fig. 3B change lens's pitch
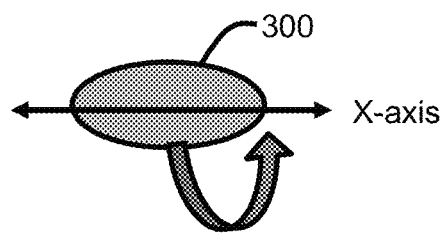
Fig. 3C Change in lens's yaw
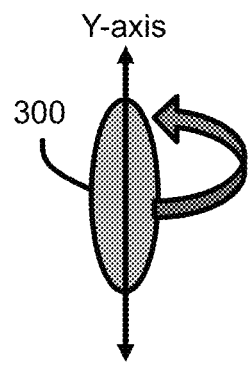

A NON-PLANAR DETECTOR

LIGHT PAINTING IMAGING DEVICE
Fig. 6A Detector Elements
Time = N
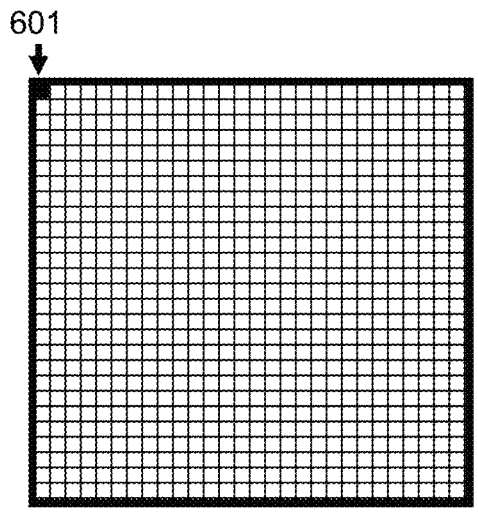
Fig. 6B Detector Elements
Time = N + 1
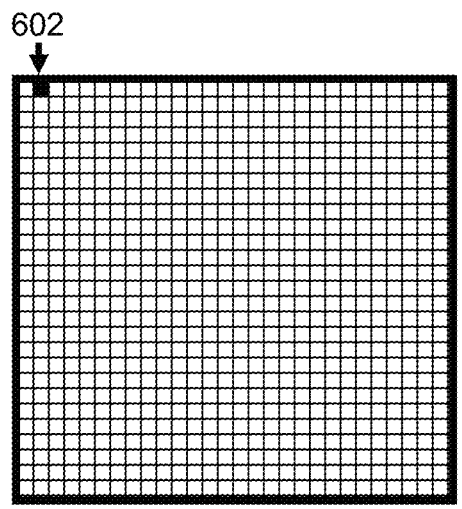
Fig. 6C Detector Elements
Time = N + 2
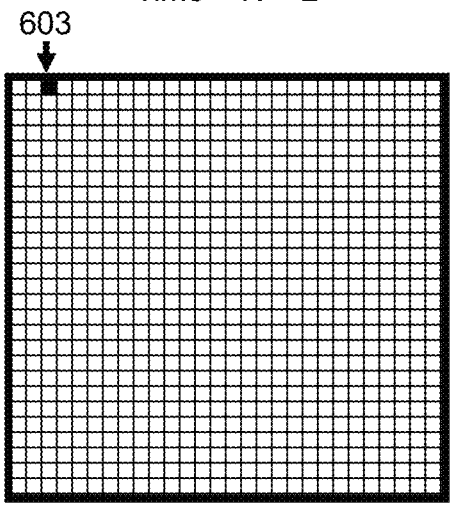
Fig. 6D Detector Elements Used
Over Time
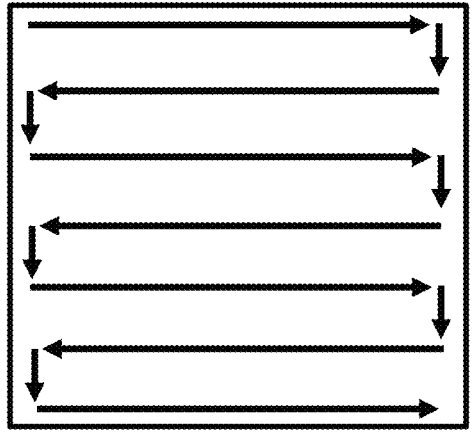

LIGHT PAINTING IMAGING DEVICE (SLPID)

OPTIMIZATION OF LENS FOR LIGHT PAINTING IMAGING DEVICE

SELECTION OF DETECTOR SIZE FOR LPDI

LIGHT PAINTING IMAGING DEVICE
Fig. 10A View from front
A time point
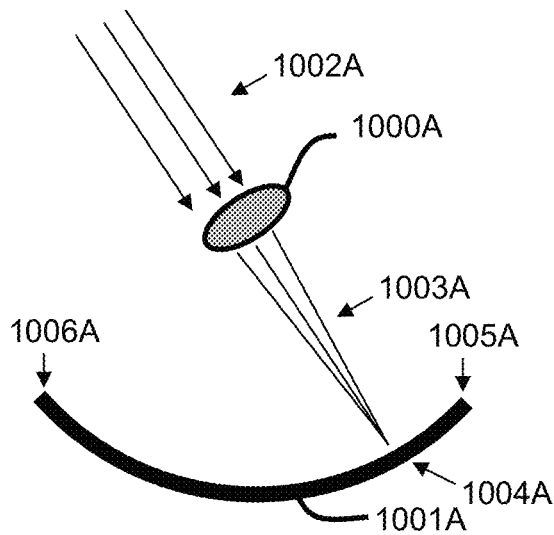
Fig. 10B View from side
A time point
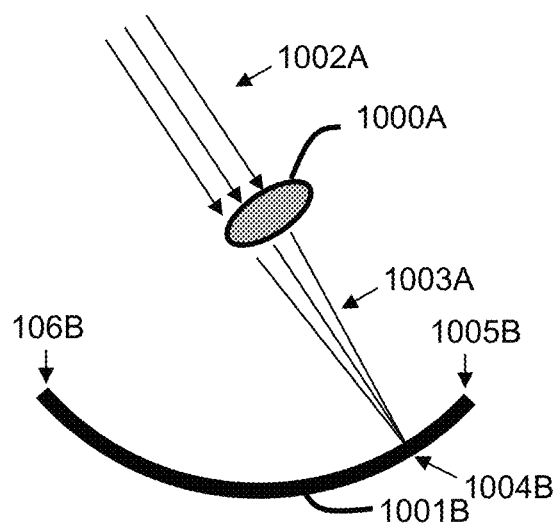
Fig. 10C View from front
A subsequent time point
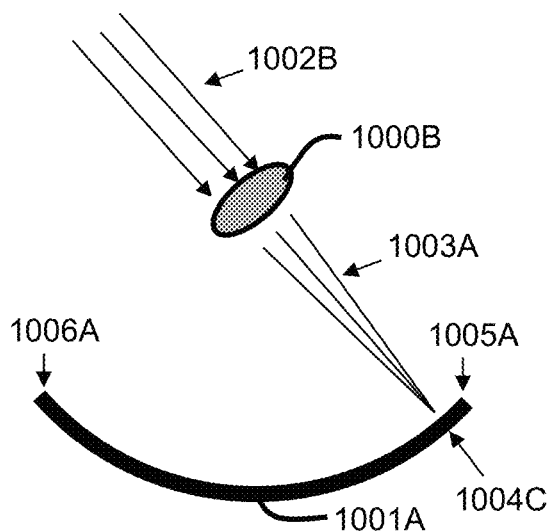
Fig. 10D View from side
A subsequent time point
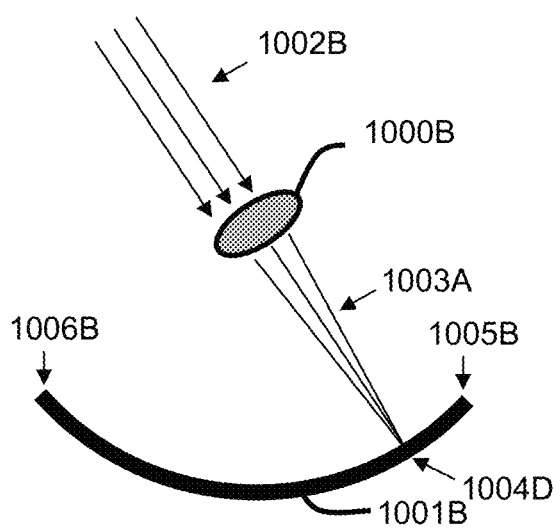

LIGHT PAINTING IMAGING DEVICE (LPID) DATA COLLECTION WITHOUT AND WITH FILTERS

FIG. 11A LPID without utilization of filters

| Detector (Row #1) | Pointing Angle | Time point, Frequency Amplitude |
|---|---|---|
| 1 | -0.499° | (1, Frequency, Amplitude) |
| 2 | -0.498° | (2, Frequency, Amplitude) |
| 3 | -0.497° | (3, Frequency, Amplitude) |
| ... | | |
| 500 | 0° | (500, Frequency, Amplitude) |
| 501 | 0.001° | (501, Frequency, Amplitude) |
| ... | | |
| 998 | 0.498° | (998, Frequency, Amplitude) |
| 999 | 0.499° | (999, Frequency, Amplitude) |
| 1000 | 0.500° | (1000, Frequency, Amplitude) |

Fig. 11B LPID with utilization of color filters

| Detector (Row #1) | Pointing Angle | Time point, Color Filter, Amplitude | Time point, Color Filter, Amplitude | Time point, Color Filter, Amplitude |
|---|---|---|---|---|
| 1 | -0.499° | (1, R, Amplitude) | (1001, G, Amplitude) | (2001, B, Amplitude) |
| 2 | -0.498° | (2, R, Amplitude) | (1002, G, Amplitude) | (2002, B, Amplitude) |
| 3 | -0.497° | (3, R, Amplitude) | (1003, G, Amplitude) | (2003, B, Amplitude) |
| ... | | | | |
| 500 | 0° | (500, R, Amplitude) | (1500, G, Amplitude) | (2500, B, Amplitude) |
| 501 | 0.001° | (501, R, Amplitude) | (1501, G, Amplitude) | (2501, B, Amplitude) |
| ... | | | | |
| 998 | 0.499° | (998, R, Amplitude) | (1998, G, Amplitude) | (2998, B, Amplitude) |
| 999 | 0.499° | (999, R, Amplitude) | (1999, G, Amplitude) | (2999, B, Amplitude) |
| 1000 | 0.500° | (1000, R, Amplitude) | (2000, G, Amplitude) | (3000, B, Amplitude) |

LIGHT PAINTING IMAGING DEVICE (LPID) PERFORMANCE CHARACTERISTICS

| Radius of curvature of the detector (in m) | Surface Area of detector array (in $m^2$) | Radius of the detector array (in $m^2$) | MP of detector array | Lens: focal length / radius of curvature | Angular resolution (pixels per degree). |
|---|---|---|---|---|---|
| 0.01 | $2.4 \times 10^{-6}$ | 0.00087 | 0.062 | 0.01 / 0.02 | 1,607 |
| 0.05 | 0.00024 | 0.0087 | 6.15 | 0.05 / 0.10 | 8,033 |
| 0.20 | 0.00096 | 0.017 | 24.67 | 0.20 / 0.40 | 32,131 |
| 0.50 | 0.0060 | 0.044 | 154.2 | 0.50 / 1.00 | 80,328 |
| 1.00 | 0.0239 | 0.087 | 616.8 | 1.00 / 2.00 | 160,655 |

Figure 12

LIGHT PAINTING IMAGING DEVICE CLUSTER (LPID-C)
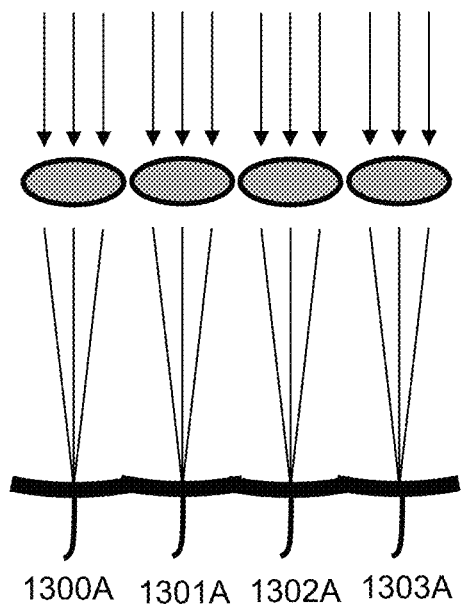
Fig. 13A View from front
A time point
1300A 1301A 1302A 1303A
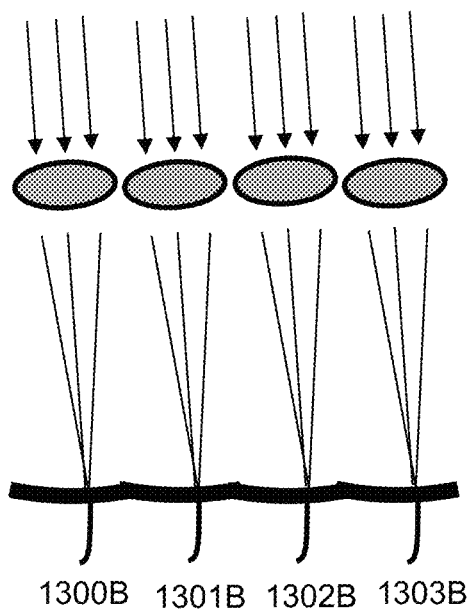
Fig. 13B View from front
Subsequent time point
1300B 1301B 1302B 1303B DEFORMABLE MIRROR YIELDING ADJUSTABLE FOCAL POINT
Fig. 17A Side view of adjustable mirror, t = N
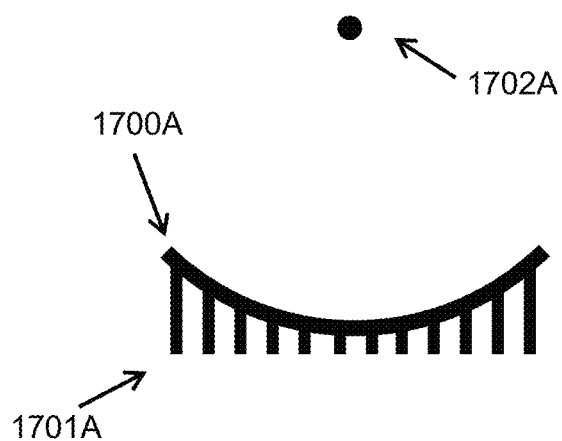
Fig. 17B Side view of adjustable mirror, t = N + 1
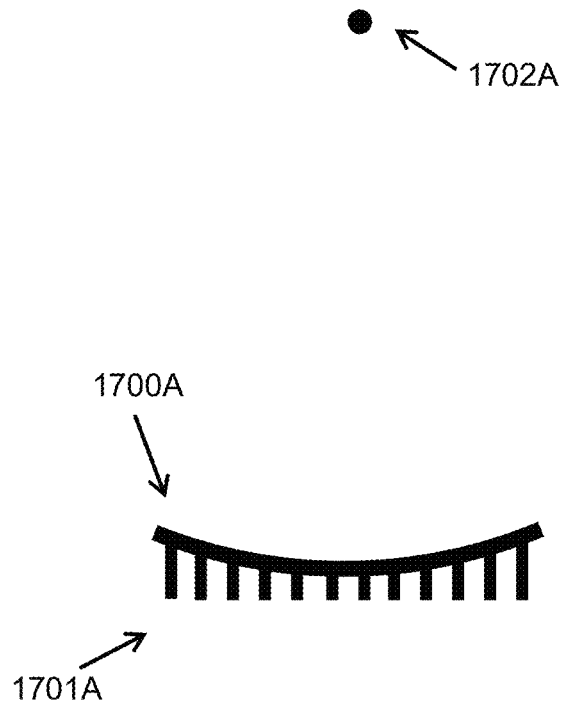

DIVERGING LENS WITH DOUBLE CURVED DETECTOR

STACKED LAYOUT FOR DETECTORS

ADAPTABLE MIRRORS AND LENSES
FIG. 20A Adaptable mirrors
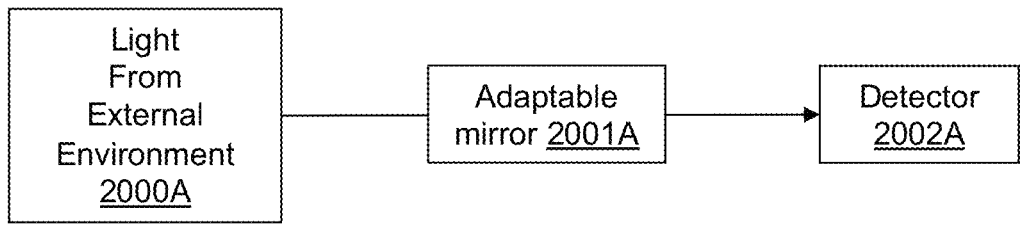
FIG. 20B Adaptable lens
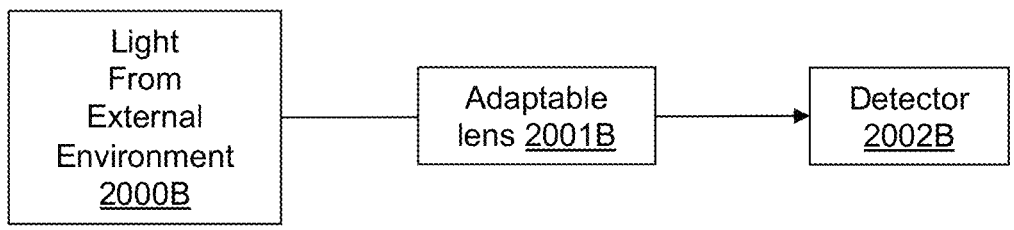
FIG. 20C Stereoscopic camera design using adaptable mirrors
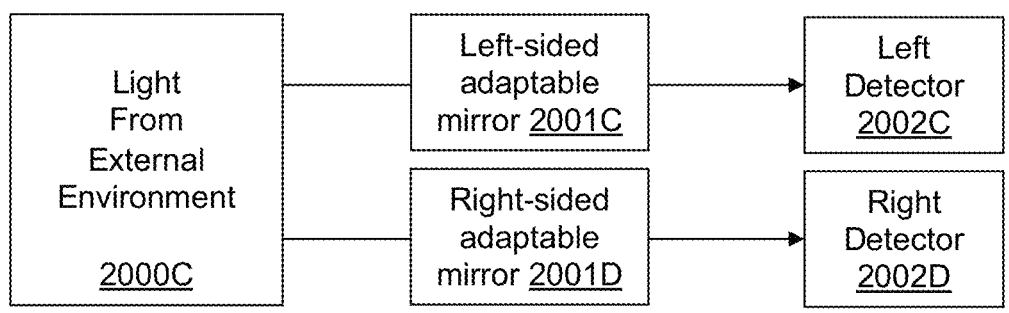
FIG. 20D Stereoscopic camera design using adaptable lenses
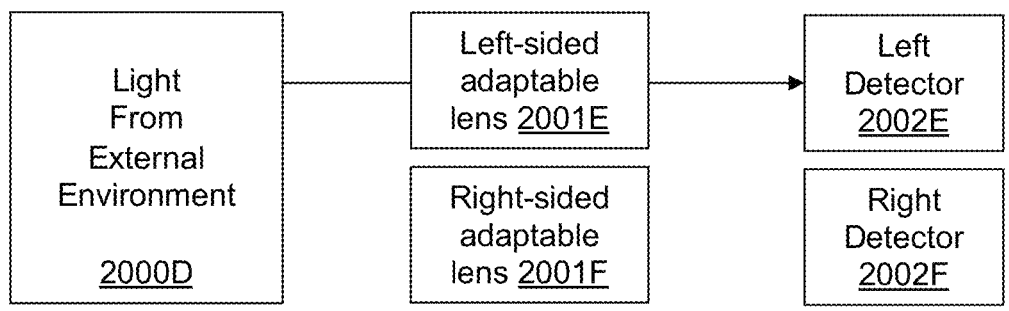

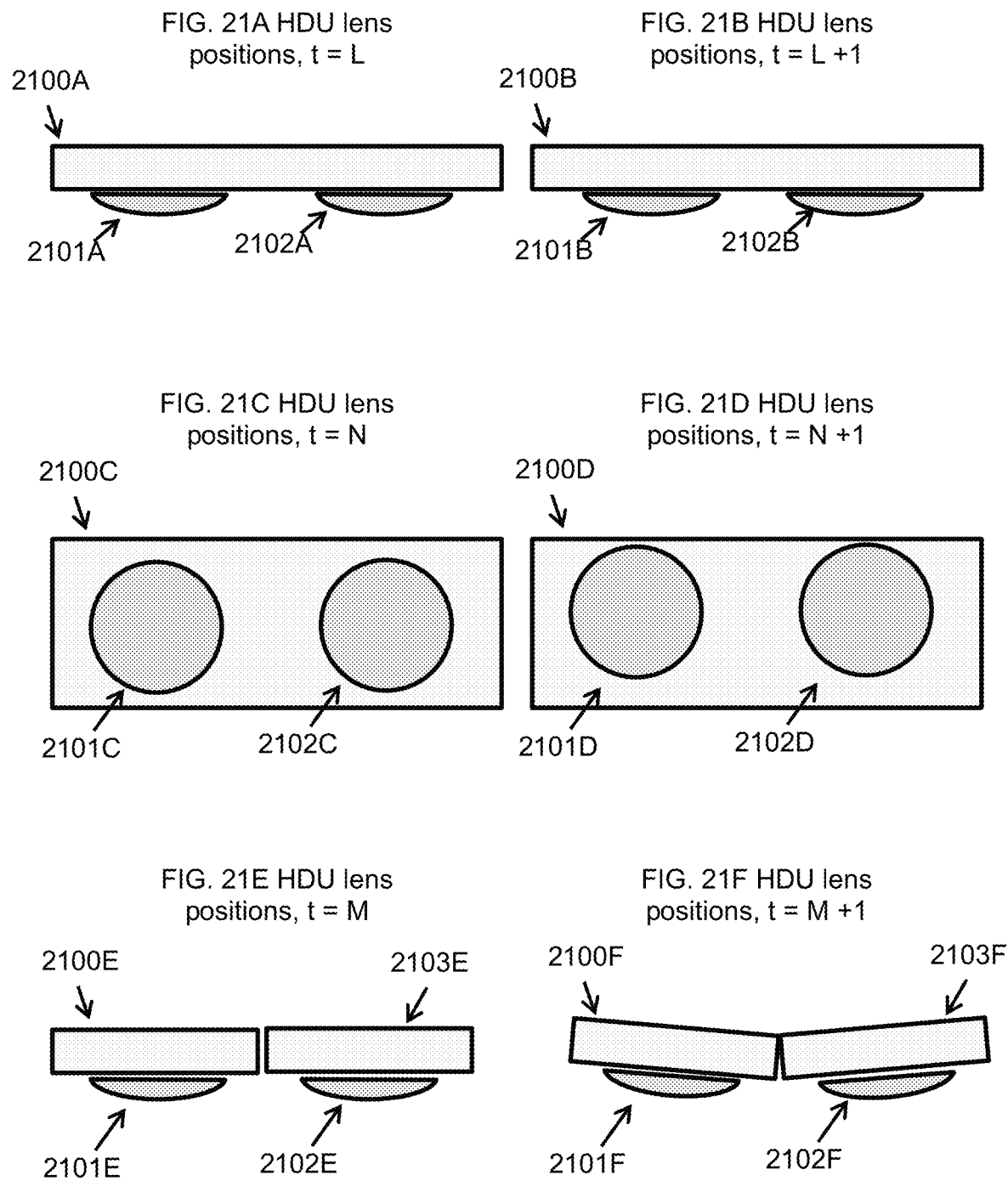

METHOD AND APPARATUS FOR IMAGING ON A DOUBLE CURVED DISPLAY

CROSS-REFERENCES TO RELATED APPLICATIONS

This patent application is a continuation-in-part of U.S. Ser. No. 17/561,961, which is incorporated by reference in its entirety.

TECHNICAL FIELD

Aspects of this disclosure are generally related to three-dimensional imaging.

BACKGROUND

Some people use stereoscopic cameras.

SUMMARY

All examples, aspects and features mentioned in this document can be combined in any technically possible way.

The key embodiments of this light painting system concept is a very high-resolution camera would include a movable sensor and lens system that paints parallel light onto the curved sensors at the focal point of the lens(s). The sensor elements would be placed on a dual curvilinear backplane for the sensor elements. This is novel in that no other 'cameras' use the focal point to capture the image—there is in all previous camera systems an offset distance from the focal point where the image is created and captured on the sensor system.

The key components of the very high-resolution light painting system would include but are not limited to: a structure which encases the parts of the camera; an optional gimbal to provide stabilization; a shutter; lens; optional mirror; optional color filters; mechanical drive system; sensor/detectors; a processor with a large memory capacity; a display; battery/power connection; a communication link; an optional geo-location system; an optional cooling system; an optional heading system; an optional range finding system; and processing options.

In some embodiments the structural component could have an attached mechanism such as a cylinder or hood to reduced cylinder stray light.

In some embodiments the optional gimbal would provide three axis stability to the very high-resolution light painting system. Due to the very narrow instantaneous field of view, a stability component may be required.

In some embodiments the shutter would provide for differing open/shut timings to include long exposure times and for tracking objects over time. The shutter would operate in conjunction with the drive system which, in turn, would direct the lens. The lens would be steerable such that the primary axis of the lens could point throughout the region of interest. In some embodiments the lens would include different shapes which would include but not be limited to: convex on both sides of the lens; concave on goth sides of the lens; a flat side in combination with either convex or concave; rectangular or circular. The shape could also include novel designs to reduce size and weight which would include a Fresnel design. The material of the lens would include but not be limited to: glass; and transparent plastics. Micro lenses could be emplaced after the primary lens to further distribute the light.

In some embodiments filters could be used in conjunction with the lens. The filter(s) would include but not be limited to color (e.g., red, green, blue); and polarized (e.g., circular, linear, anaglyph).

In some embodiments, mirrors (optional) would be included within the overall the very high-resolution light painting system. The mirrors would redirect the light form the lens to the sensor/detector array. The mirrors could be stationary and of different shapes (e.g., flat, curvilinear). Alternatively, could be fast scanning mirrors, operating in conjunction with the drive system. These mirrors would provide a back scan capability which would reduce the time to scan the area of interest.

The sensor/detector array is central to the very high-resolution light painting concept. The unique shape of the sensor/detector array is that it is curved along two axis to match the focal point of the primary direction of the lens as it rotates in two axis to cover the user specified area of interest. Note that the lens focal point is continuously on the sensor/detector array throughout the camera system cycle of obtaining a single frame of imagery of the region of interest or multiple sequential frames tracking an object of interest.

A processor will direct the movable components within very high-resolution light painting system. The processor will also direct collection of data from the sensor/detector array and send it to the system memory. This data will also be sent to the very high-resolution light painting system interactive display. The interactive display will enable: viewing of the current imagery; previously recorded imagery; and, pull down menus with user selectable system settings. The settings would also include provisions for downloading the images to external sources (e.g., internet. memory devices, etc.). Power for the system could be a rechargeable battery or external source.

In some embodiments, optional linkages from the very high-resolution light painting system to the external environment could be provided. These linkages could include but would not be limited to: global positioning system (GPS); laser range finger (LRF); digital compass (DC); internal clock; attitude and heading system. There could be combination of these linkages. For example, from a known GPS location in combination with DC and the LRF, the GPS location of a distant object could be computed. During nighttime, the AHS in conjunction with the clock and linkage to a star gazers map could permit observation, for example, observation of Mars moons.

In some embodiments, additional processing capabilities could be added to the processor. An example would be automatic object recognition. Faces along with a person's data and when the very high-resolution light painting system was pointed at a person, the display could provide the data.

In some embodiments, scalability of the very high-resolution light painting system can be implemented. If one envisions a cone inside a sphere wherein the apex of the cone is located at the center of the sphere, then for different radii of curvature of the sphere the f-number will grow in consonance with the radii.

In some embodiments, different types of aberrations can the addressed. Consider spherical aberrations. For spherical lenses, which are cheaper to produce, only the center portion of the lens correctly places the light rays at the focal point. For the very high-resolution light painting system, spherical aberrations can produce erroneous pixels within the images. This can be reduced through use of multiple lenses. Alternatively, aspheric can employed. Next consider chromatic aberrations wherein light rays of different colors (frequencies) bend at differing angles as they pass through a lens.

Thus, these light rays of different colors do not intersect at the same focal point. For the very high-resolution light painting system, chromatic aberrations can produce erroneous color of pixels in the outer portion of images. This can be corrected to some degree through the use of tow or more lenses with different refractive indices. Image processing can help correct chromatic aberrations.

In some embodiments, different types of distortions can the addressed. Consider barrel distortions wherein, for wide angles, the image tends to bow out. For the very high-resolution light painting system, barrel distortions can be reduced through image processing. The image processing applies a corrective factor based on the distance form the center of the image for each pixel. Next consider pincushion distortion wherein images get pinched in the center. For the very high-resolution light painting system, barrel distortions can be reduced through image processing. In this case the magnification increases with the distance from the center of the image. A corrective factor can be applied based of the pixel distance from the center.

In some embodiments, alternative modes of operation will be user selectable for the very high-resolution light painting system. These include but are not limited to: single frame of imagery; selectable number of frames; motion picture mode; pan mode for wide area coverage with interaction with the gimbal, as needed for area coverage; long duration exposure mode; object tracking mode with feedback to gimbal for corrective realignment, as needed.

In some embodiments, image storage for the very high-resolution light painting system will be considered. Depending on the number of pixels within the system and the intended mode(s) of operation, there can be terabytes or gigabytes or more of data requiring storage. Flash drives integral to the very high-resolution light painting system can store terabytes of data. For large systems, the data could be transferred to external memory racks. Linkages to the cloud could be made to periodically upload the data to the cloud. Image compression techniques can be employed. This would include but not be limited to joint photographic experts group (JPEG); portable network graphics (PNG); graphics interchange format (GIF); and tag image file format (TIFF), etc. Another technique would be for the user to change the number of bits being stored for color images. Options include 16-bit; 24-bit and 32-bit data.

In some embodiments, cooling for the very high-resolution light painting system will be considered. In small systems, an internal fan might be sufficient. For large system, however, an external cooling system may be required.

In some embodiments, stereoscopic viewing of the virtual 3D mannequin is performed on an extended reality display unit, which is described in U.S. Pat. No. 8,384,771, METHOD AND APPARATUS FOR THREE DIMIENSIONAL VIEWING OF IMAGES, which is incorporated by reference in its entirety. This patent teaches image processing techniques including volume generation, filtering, rotation, and zooming.

In some embodiments, stereoscopic viewing of the virtual 3D mannequin is performed with convergence, which is described in U.S. Pat. No. 9,349,183, METHOD AND APPARATUS FOR THREE DIMIENSIONAL VIEWING OF IMAGES, which is incorporated by reference in its entirety. This patent teaches shifting of convergence. This feature can be used in combination with filtering.

In some embodiments, stereoscopic viewing can be performed using a display unit, which incorporates polarized lenses, which is described in U.S. Pat. No. 9,473,766, METHOD AND APPARATUS FOR THREE DIMIENSIONAL VIEWING OF IMAGES, which is incorporated by reference in its entirety.

In some embodiments, advancements to display units can be incorporated for viewing the virtual 3D mannequin, which are taught in U.S. patent application Ser. No. 16/828,352, SMART GLASSES SYSTEM and U.S. patent application Ser. No. 16/997,830, ADVANCED HEAD DISPLAY UNIT FOR FIRE FIGHTERS, which are both incorporated by reference in their entirety.

In some embodiments, advancements in display units are taught in U.S. patent application Ser. No. 17/120,109, ENHANCED VOLUME VIEWING, which is incorporated by reference in its entirety. Included herein is a head display unit, which is improved by incorporating geo-registration.

Some embodiments comprise utilizing an improved field of view on an extended reality head display unit, which is taught in U.S. patent application Ser. No. 16/893,291, A METHOD AND APPARATUS FOR A HEAD DISPLAY UNIT WITH A MOVABLE HIGH RESOLUTION FIELD OF VIEW, which is incorporated by reference in its entirety.

In some embodiments, image processing steps can be performed using a 3D volume cursor, which is taught in U.S. Pat. No. 9,980,691, METHOD AND APPARATUS FOR THREE DIMIENSIONAL VIEWING OF IMAGES, and U.S. Pat. No. 10,795,457, INTERACTIVE 3D CURSOR, both of which are incorporated by reference in its entirety.

In some embodiments, a precision sub-volume can be utilized in conjunction with the virtual 3D mannequin, which is taught in U.S. patent application Ser. No. 16/927,886, A METHOD AND APPARATUS FOR GENERATING A PRECISION SUB-VOLUME WITHIN THREE-DIMENSIONAL IMAGE DATASETS, which is incorporated by reference in its entirety.

In some embodiments, viewing of a structure at two different time points can be performed using a ghost imaging technique, which is taught in U.S. Pat. No. 10,864,043, INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING, which is incorporated by reference in its entirety.

Some embodiments comprise selecting a specific surgical device for pre-operative planning, which is taught in U.S. patent application Ser. No. 17/093,322, A METHOD OF SELECTING A SPECIFIC SURGICAL DEVICE FOR PREOPERATIVE PLANNING, which is incorporated by reference in its entirety.

Some embodiments comprise, generating the virtual 3D mannequin using techniques described in U.S. patent application Ser. No. 16/867,102, METHOD AND APPARATUS OF CREATING A COMPUTER-GENERATED PATIENT SPECIFIC IMAGE, which is incorporated by reference in its entirety. Key techniques include using patient factors (e.g., history, physical examination findings, etc.) to generate a volume.

Some embodiments comprise advanced image processing techniques available to the user of the virtual 3D mannequin, which are taught in U.S. Pat. No. 10,586,400, PROCESSING 3D MEDICAL IMAGES TO ENHANCE VISUALIZATION, and U.S. Pat. No. 10,657,731, PROCESSING 3D MEDICAL IMAGES TO ENHANCE VISUALIZATION, both of which are incorporated by reference in its entirety.

Some embodiments comprise performing voxel manipulation techniques so that portions of the virtual 3D mannequin can be deformed and move in relation to other portions of the virtual 3D mannequin, which is taught in U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, which is incorporated by reference in its entirety.

Some embodiments comprise generating at least some portions of the virtual 3D mannequin through artificial intelligence methods and performing voxel manipulation thereof, which is taught in U.S. patent application Ser. No. 16/736,731, RADIOLOGIST-ASSISTED MACHINE LEARNING WITH INTERACTIVE, VOLUME SUBTENDING 3D CURSOR, which is incorporated by reference in its entirety.

Some embodiments comprise wherein at least some component of the inserted 3D dataset into the virtual 3D mannequin are derived from cross-sectional imaging data fine tuned with phantoms, which is taught in U.S. patent application Ser. No. 16/752,691, IMPROVING IMAGE QUALITY BY INCORPORATING DATA UNIT ASSURANCE MARKERS, which is incorporated by reference in its entirety.

Some embodiments comprise utilizing halo-type segmentation techniques, which are taught in U.S. patent application Ser. No. 16/785,606, IMPROVING IMAGE PROCESSING VIA A MODIFIED SEGMENTED STRUCTURE, which is incorporated by reference in its entirety.

Some embodiments comprise using techniques for advanced analysis of the virtual 3D mannequin taught in U.S. patent application Ser. No. 16/939,192, RADIOLOGIST ASSISTED MACHINE LEARNING, which are incorporated by reference in its entirety.

Some embodiments comprise performing smart localization from a first virtual 3D mannequin to a second virtual 3D mannequin, such as in an anatomy lab, which is performed via techniques taught in U.S. patent application Ser. No. 17/100,902, METHOD AND APPARATUS FOR AN IMPROVED LOCALIZER FOR 3D IMAGING, which is incorporated by reference in its entirety.

Some embodiments comprise performing a first imaging examination with a first level of mechanical compression and a second imaging examination with a second level of mechanical compression and analyzing differences therein, which is taught in U.S. patent application Ser. No. 16/594,139, METHOD AND APPARATUS FOR PERFORMING 3D IMAGING EXAMINATIONS OF A STRUCTURE UNDER DIFFERING CONFIGURATIONS AND ANALYZING MORPHOLOGIC CHANGES, which is incorporated by reference in its entirety.

Some embodiments comprise displaying the virtual 3D mannequin in an optimized image refresh rate, which is taught in U.S. patent application Ser. No. 16/842,631, A SMART SCROLLING SYSTEM, which is incorporated by reference in its entirety.

Some embodiments comprise displaying the virtual 3D mannequin using priority volume rendering, which is taught in U.S. Pat. No. 10,776,989, A METHOD AND APPARATUS FOR PRIORITIZED VOLUME RENDERING, which is incorporated by reference in its entirety.

Some embodiments comprise displaying the virtual 3D mannequin using tandem volume rendering, which is taught in U.S. patent Ser. No. 17/033,892, A METHOD AND APPARATUS FOR TANDEM VOLUME RENDERING, which is incorporated by reference in its entirety.

Some embodiments comprise displaying images in a optimized fashion by incorporating eye tracking, which is taught in U.S. patent application Ser. No. 16/936,293, IMPROVING VISUALIZATION OF IMAGES VIA AN ENHANCED EYE TRACKING SYSTEM, which is incorporated by reference in its entirety.

Some embodiments comprise enhancing collaboration for analysis of the virtual 3D mannequin by incorporating teachings from U.S. patent application Ser. No. 17/072,350, OPTIMIZED IMAGING CONSULTING PROCESS FOR RARE IMAGING FINDINGS, which is incorporated by reference in its entirety.

Some embodiments comprise improving multi-user viewing of the virtual 3D mannequin by incorporating teachings from U.S. patent application Ser. No. 17/079,479, AN IMPROVED MULTI-USER EXTENDED REALITY VIEWING TECHNIQUE, which is incorporated by reference in its entirety.

Some embodiments comprise improving analysis of images through use of geo-registered tools, which is taught in U.S. Pat. No. 10,712,837, USING GEO-REGISTERED TOOLS TO MANIPULATE THREE-DIMENSIONAL MEDICAL IMAGES, which is incorporated by reference in its entirety.

Some embodiments comprise integration of virtual tools with geo-registered tools, which is taught in U.S. patent application Ser. No. 16/893,291, A METHOD AND APPARATUS FOR THE INTERACTION OF VIRTUAL TOOLS AND GEO-REGISTERED TOOLS, which is incorporated by reference in its entirety.

In some embodiments blood flow is illustrated in the virtual 3D mannequin, which is taught in U.S. patent application Ser. No. 16/506,073, A METHOD FOR ILLUSTRATING DIRECTION OF BLOOD FLOW VIA POINTERS, which is incorporated by reference in its entirety and U.S. Pat. No. 10,846,911, 3D IMAGING OF VIRTUAL FLUIDS AND VIRTUAL SOUNDS, which is also incorporated by reference in its entirety.

Some embodiments also involve incorporation of 3D printed objects to be used in conjunction with the virtual 3D mannequin. Techniques herein are disclosed in U.S. patent Ser. No. 17/075,799, OPTIMIZING ANALYSIS OF A 3D PRINTED OBJECT THROUGH INTEGRATION OF GEO-REGISTERED VIRTUAL OBJECTS, which is incorporated by reference in its entirety.

Some embodiments also involve a 3D virtual hand, which can be geo-registered to the virtual 3D mannequin. Techniques herein are disclosed in U.S. patent application Ser. No. 17/113,062, A METHOD AND APPARATUS FOR A GEO-REGISTERED 3D VIRTUAL HAND, which is incorporated by reference in its entirety.

Some embodiments comprise utilizing images obtained from U.S. patent application Ser. No. 16/654,047, METHOD TO MODIFY IMAGING PROTOCOLS IN REAL TIME THROUGH IMPLEMENTATION OF ARTIFICIAL, which is incorporated by reference in its entirety.

Some embodiments comprise utilizing images obtained from U.S. patent application Ser. No. 16/597,910, METHOD OF CREATING AN ARTIFICIAL INTELLIGENCE GENERATED DIFFERENTIAL DIAGNOSIS AND MANAGEMENT RECOMMENDATION TOOL BOXES DURING MEDICAL PERSONNEL ANALYSIS AND REPORTING, which is incorporated by reference in its entirety.

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides steps explained herein that when performed (e.g. when executing) on the processor, operates as explained herein within the computerized device to perform all of the method embodiments and operations explained herein as embodiments of the invention. Thus any computerized device that performs or is programmed to perform processing explained herein is an embodiment of the invention.

Other arrangements of embodiments of the invention that are disclosed herein include Software programs to perform the method embodiment steps and operations Summarized above and disclosed in detail below. More particularly, a computer program product is one embodiment that has a computer-readable medium including computer program logic encoded thereon that when performed in a computerized device provides associated operations providing steps as explained herein.

The computer program logic, when executed on at least one processor with a computing system, causes the processor to perform the operations (e.g., the methods) indicated herein as embodiments of the invention. Such arrangements of the invention are typically provided as Software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other Such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as Software and hardware, or as hardware and/or circuitry alone. Such as within a data communications device. The features of the invention, as explained herein, may be employed in data processing devices and/or Software systems for Such devices. Note that each of the different features, techniques, configurations, etc. discussed in this disclosure can be executed independently or in combination. Accordingly, the present invention can be embodied and viewed in many different ways. Also, note that this Summary section herein does not specify every embodiment and/or incrementally novel aspect of the present disclosure or claimed invention. Instead, this Summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE FIGURES

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 illustrates design features of the light painting imaging device.

FIG. 3A illustrates the coordinate system for the lens.

FIG. 3B illustrates wherein the lens undergoes a change in its pitch.

FIG. 3C illustrates pitching of the lens.

FIG. 6A illustrates the detector array's elements at time equals N.

FIG. 6B illustrates the detector array's elements at time equals N+1.

FIG. 6C illustrates the detector array's elements at time equals N+2.

FIG. 6D illustrates the detector array's elements used over time.

FIG. 10A illustrates a front view of a light painting imaging device at a time point.

FIG. 10B illustrates a side view of a light painting imaging device at the time point in FIG. 10A.

FIG. 10C illustrates a front view of a light painting imaging device at a subsequent time point.

FIG. 10D illustrates a side view of a light painting imaging device at the subsequent time point in FIG. 10C.

FIG. 11A illustrates data collection from a light painting imaging device (LPID) without filters.

FIG. 11B illustrates data collection from a light painting imaging device (LPID) with filters.

FIG. 12 illustrates the light painting imaging device (LPID) performance characteristics.

FIG. 13A illustrates a light painting imaging device cluster at a time point.

FIG. 13B illustrates the light painting imaging device cluster at a subsequent time point.

FIG. 17A illustrates a deformable mirror yielding a first focal point.

FIG. 17B illustrates a deformable mirror yielding a second focal point.

FIG. 20A illustrates the adaptable mirror concept.

FIG. 20B illustrates the adaptable lens concept.

FIG. 20C illustrates a camera design with stereoscopic adaptable mirrors.

FIG. 20D illustrates a camera design with stereoscopic adaptable lenses.

FIG. 21A illustrates head display unit lens positions at time=L.

FIG. 21B illustrates head display unit lens positions at time=L+1.

FIG. 21C illustrates head display unit lens positions at time=M.

FIG. 21D illustrates head display unit lens positions at time=M+1.

FIG. 21E illustrates head display unit lens orientations at time=N.

FIG. 21F illustrates head display unit lens orientations at time=N+1.

DETAILED DESCRIPTION

Figure 2:
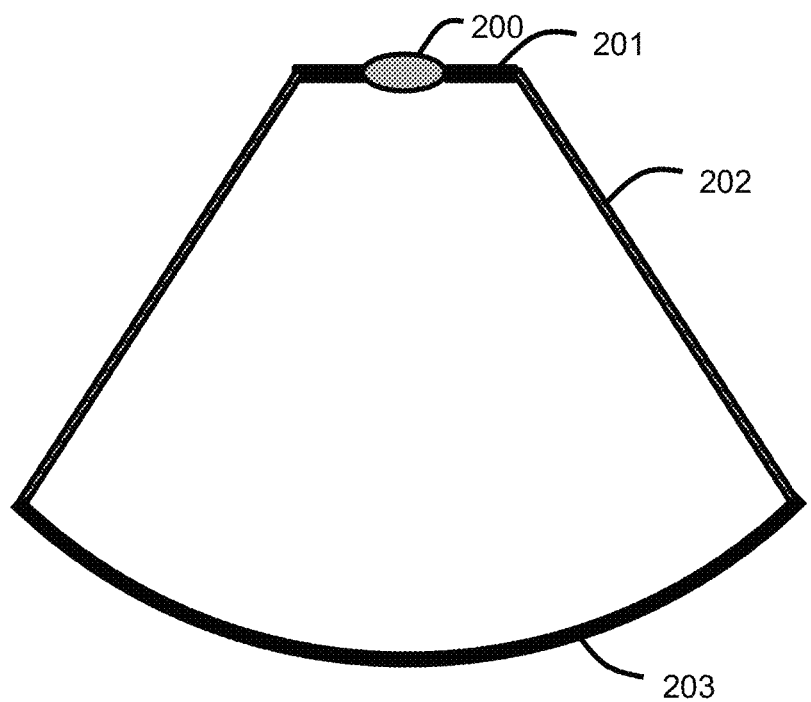
FIG. 2 illustrates the light painting imaging device.

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

FIG. 1 illustrates design features of the light painting imaging device (LPID) 100 illustrates a text box highlighting key design features. In the preferred embodiment, which is the LPID, the lens is positioned on a bi-axial rotatable mount. The preferred embodiment is a fast rotation speed about a first axis and a slow rotation speed about a second axis. Center of rotation is about the center of the lens. The preferred embodiment is a converging lens. Alternative embodiments include a Fresnel lens or a diverging lens.

Next, is a detector array (sensor). The type can be a CMOS (complementary metal oxide semiconductor) or CCD (charge coupled device). The preferred embodiment is a shape, which is curved wherein the center point of the lens is equidistant to all points on the detector array. Other embodiment comprises a stacked layout, which is when more than one detector are aligned with the principal axis of a lens. Other embodiments include composite construction. Lens options: Fresnel, Converging. Materials can be glass or plastic. Other features include: a processor; a memory; filters; microlenses; LIDAR/LRF; shutter(s); cover(s) to reduce ambient light; precision timing for data recording (data from only a single detector element or set of detector elements is recorded at a time epoch). Some embodiments comprise performing calibration of the system with light sources. Some embodiments comprise performing registration of imagery with GPS or reference points (e.g., North Star). Some embodiments comprise using multiple units including a cluster of units from a single viewing perspective; and, a first imaging set at a first location; second imaging set at a second imaging location for stereoscopic. Some embodiments comprise using a display (flat monitor; Extended Reality head display unit; double curved display per U.S. Ser. No. 17/561,961, A method and apparatus of presenting 2D images on a double curved, non-planar display, which is incorporated by reference in its entirety). Note that the curved detector can be partial spherical in shape. The orientation of the apex of the detector can be located on the side closest to the center of the lens or on the side farthest from the center of the lens. Techniques described herein can be used for a telescope, telephoto lens, microscope or other types of photography or videography.

FIG. 2 illustrates the light painting imaging device. 200 illustrates a converging lens. 201 illustrates a mount for the converging lens 200. In the preferred embodiment, this lens can rotate about two axes. 202 illustrates housing for blocking ambient light. This can be made of opaque material. 203 illustrates a detector. Note that each of the detector elements along the detector are locate at the focal point of the converging lens 200. In the preferred embodiment, the surface of the detectors are located at the focal point of the converging lens. As the lens rotates via pitch and yaw about the center of the lens, the focal point of the lens moves to different detectors along the non-planar detector. Additionally, the lens is positioned such that its focal point lands on the detector. Additionally, the shape of the non-planar detector has a curvature to match the focal length of the lens.

FIG. 3A illustrates the coordinate system for the lens. 300 illustrates a lens. In the preferred embodiment, a converging lens is used. This can be a biconvex lens. The x-axis is illustrated. The y-axis is illustrated.

FIG. 3B illustrates wherein the lens undergoes a change in its pitch. 300A illustrates the lens, which is now in a different orientation as compared to FIG. 3A. The x-axis is illustrated. The arrow illustrates pitch about the x-axis. The preferred units for pitch is degrees. In the preferred embodiment, 0 degrees of pitch would be when the lens's focal point is at the horizontal midline of the detector. Positive lens pitch would correspond to where the focal point is at the upper half of the detector. Negative lens pitch would correspond to where the focal point is at the lower half of the detector.

FIG. 3C illustrates pitching of the lens. The y-axis is illustrated. 300A illustrates the lens, which is now in a different orientation as compared to FIG. 3A. The arrow illustrates yaw about the y-axis. The preferred units for yaw is degrees. In the preferred embodiment, 0 degrees of yaw would be when the lens's focal point is at the vertical midline of the detector. Positive lens yaw would correspond to where the focal point is at the right side of the detector. Negative lens yaw would correspond to where the focal point is at the left side of the detector. Thus, 0 degrees of pitch and 0 degrees of yaw would correspond to the midpoint of the detector. Combinations of pitch and yaw can be achieved. This can allow the lens's focal point to be located at any point in the detector.

Figure 4A:
FIG. 4A is a top view of a non-planar detector.

FIG. 4A is a top view of a non-planar detector.

Figure 4B:
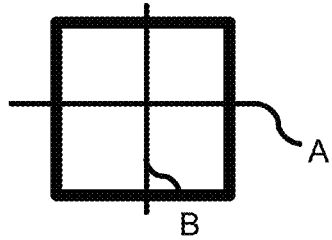
FIG. 4B is a front view of the non-planar detector shown in FIG. 4A.

FIG. 4B is a front view of the non-planar detector shown in FIG. 4A.

Note a cross-section taken along line A. Note a cross-section taken along line B.

Figure 4C:
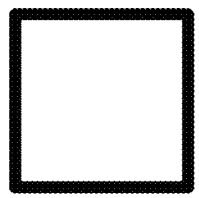
FIG. 4C is a rear view of the non-planar detector shown in FIG. 4A.

FIG. 4C is a rear view of the non-planar detector shown in FIG. 4A.

Figure 4D:
FIG. 4D is the right-side view of the non-planar detector shown in FIG. 4A.

FIG. 4D is the right side view of the non-planar detector shown in FIG. 4A.

Figure 4E:
FIG. 4E is the left-side view of the non-planar detector shown in FIG. 4A.

FIG. 4E is the left side view of the non-planar detector shown in FIG. 4A.

Figure 4F:
FIG. 4F is the bottom view of the non-planar detector shown in FIG. 4A.

FIG. 4F is the bottom view of the non-planar detector shown in FIG. 4A.

Figure 4G:
FIG. 4G is a cross-sectional view taken along line A in FIG. 4B.

FIG. 4G is a cross-sectional view taken along line A in FIG. 4B.

Figure 4H:
FIG. 4H is a cross-sectional view taken along line B in FIG. 4B.

FIG. 4H is a cross-sectional view taken along line B in FIG. 4B. The device is not limited to the scale shown herein. Also note that the top, bottom, left and right sides of the monitor can be comprised of straight edges or curved edges. The uniqueness of this design is the "double curved" appearance. Note that the top portion of the monitor curves inwards towards the lens of the light painting imaging device (LPID). Note that the bottom portion of the monitor curves inwards towards the LPID. Note that the left portion of the monitor curves inward towards the LPID. Note that the right portion of the monitor curves inward towards the LPID. The curvatures are designed to be in proximity to the focal point of the lens, which as the lens rotates about its center, the focal point moves along the double curved, non-planar detector. In some embodiments, the 2D image can be derived from imagery as described in Ser. No. 17/225,610 filed on Apr. 8, 2021, AN IMPROVED IMMERSIVE VIEWING EXPERIENCE, which is incorporated by reference in its entirety and Ser. No. 17/237,152 filed on Apr. 22, 2021, AN IMPROVED IMMERSIVE VIEWING EXPERIENCE, which is incorporated by reference in its entirety.

Figure 5:
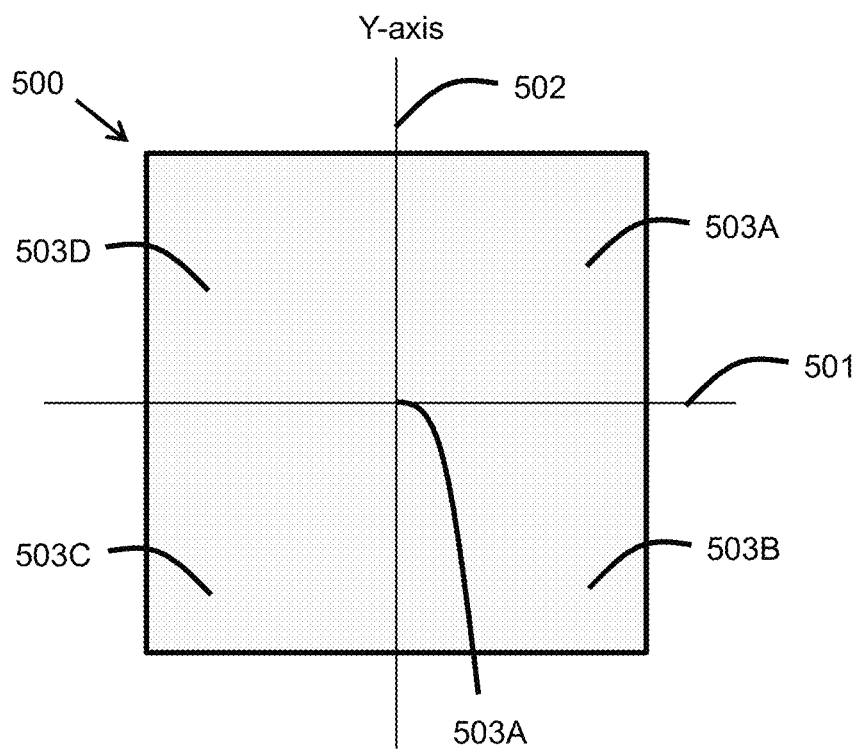
FIG. 5 illustrates a coordinate system for the detector.

FIG. 5 illustrates a coordinate system for the detector. 500 illustrates a front view of the detector. 501 illustrates the horizontal midline of the detector, which would correspond to 0 degrees of pitch. 502 illustrates the vertical midline of the detector, which would correspond to 0 degrees of yaw. 503A illustrates the quadrant wherein there is positive pitch and positive yaw. 503B illustrates the quadrant wherein there is negative pitch and positive yaw. 503C illustrates the quadrant wherein there is negative pitch and negative yaw. 503D illustrates the quadrant wherein there is positive pitch and negative yaw. Each coordinate on the grid corresponds to a direction from which the imaging device is pointed. Some embodiments comprise using a single detector. Some embodiments comprise using a composite detector wherein the composite detector is comprised of multiple adjacent detectors. If a composite detector is used, the images from each detector can be stitched together to generate a composite image.

FIG. 6A illustrates the detector array's elements at time equals N. 601 illustrates the first detector element in the detector array, which is the location where the focal point is located at the first time point time=N. This detector element corresponds to the principal axis of the lens at time point N+1. A novel aspect is using this feature to generate an image of an environment, such as an image of space objects (the Moon, Mars, Saturn, Jupiter's moons, etc.) or land features (people, forests, buildings and other objects). In some embodiments, more than one detector element is illuminated by the focal spot at a time point. In some embodiments, a timing system is used wherein data is only collected at a predetermined detector element that matches a timing scheme. For example, at time point N, only data at detector row #1, column #1 is collected and data at other detector elements is filtered. In some embodiments a cluster of more than one detector elements is used over time.

FIG. 6B illustrates the detector array's elements at time equals N+1. 602 illustrates the second element in the detector array, which is the location where the focal point is located at the first time point time=N+1. This detector element corresponds to the principal axis of the lens at time point N+1. In some embodiments, more than one detector element is illuminated by the focal spot at a time point. In some embodiments, a timing system is used wherein data is only collected at a predetermined detector element that matches a timing scheme. For example, at time point N+1, only data at detector row #1, column #2 is collected and data at other detector elements is filtered. In some embodiments a cluster of more than one detector elements is used over time.

FIG. 6C illustrates the detector array's elements at time equals N+2. 603 illustrates the third element in the detector array, which is the location where the focal point is located at the first time point time=N+1. This detector element corresponds to the principal axis of the lens at time point N+1. In some embodiments, more than one detector element is illuminated by the focal spot at a time point. In some embodiments, a timing system is used wherein data is only collected at a predetermined detector element that matches a timing scheme. For example, at time point N+2, only data at detector row #1, column #3 is collected and data at other detector elements is filtered. In some embodiments a cluster of more than one detector elements is used over time. So, when the lens is in a first position, data from a first detector element is recorded. When the lens is in a second position, data from a second detector element is recorded. When the lens is in a third position, data from a third detector element is recorded. In the preferred embodiment, a double curved detector is used. An novel aspect of the double curved detector is the elimination of pincushion with telephoto lenses and barrel distortion with wide angle lenses. This detector is shaped as a section of a sphere and has been described in U.S. Ser. No. 17/561,961, A METHOD AND APPARATUS OF PRESENTING 2D IMAGES ON A DOUBLE CURVED, NON-PLANAR DISPLAY, which is incorporated by reference in its entirety.

FIG. 6D illustrates the detector array's elements used over time. The arrows are illustrative to show the pattern of scanning. A variety of light painting patterns can be performed. In the preferred embodiment, the scanning pattern is driven by the fast rotation rate about a first axis of the lens (a yaw rotation) accounting for the focal spot moving across the rows and a slow rotation rate of a second axis of the lens about a second axis of the lens (a pitch rotation) accounting for the focal spot moving downward across the columns. So, the fast yaw would bring the focal spot all the way across the detector array's first row. Then the slow pitch would bring the focal point downward and the fast yaw would bring the focal point back across the row below and in an opposite direction. In the preferred embodiment, the lens rotates about the center point of the lens. Since the rotation rates vary, a snake-like pattern is generates. The actual position of the focal point would smoothly move with smooth curves. A novel aspect of this invention is wherein the orientation of the lens relative to the detector is changing. In the preferred embodiment, the center of the lens is in a fixed location relative to the detector. FIG. 6D is illustrative only. So, lots of light from a single dot in the distance onto one detector element at a given time point and this is novel as it provides improved spatial resolution and sufficient illumination for image generation. In some embodiments, the focal spot can move over detector elements (so light moves over and "paints") a set of detector elements and can move over the same detector elements to "repaint" and "repaint" again a small spot for video-like imagery. In the preferred embodiment, the apparatus called the light painting imaging device is fixed in position, such as on an observatory. In some embodiments, the entire light painting imaging system can be placed on a movable or rotatable structure. This novel aspect allows "re-paint" the same grid with the new imaging field of view (e.g., sector of sky). So, the imaging apparatus can first capture extremely high resolution imagery of an area of the environment (northern direction). Then, the imaging apparatus can maneuver by changing position or orientation to a new area of the environment (eastern direction) and repeat the imagery. Then, the images can be stitched together for a composite image. So, in some embodiments, the apparatus can be placed on a rotatable mount. So, in some embodiments, the apparatus moves to a first orientation and then stops and images. Then, the apparatus moves to a second orientation and then stops and images again. This aspect is called a swivel camera wherein the entire camera apparatus is placed on a rotatable mount.

Figure 7:
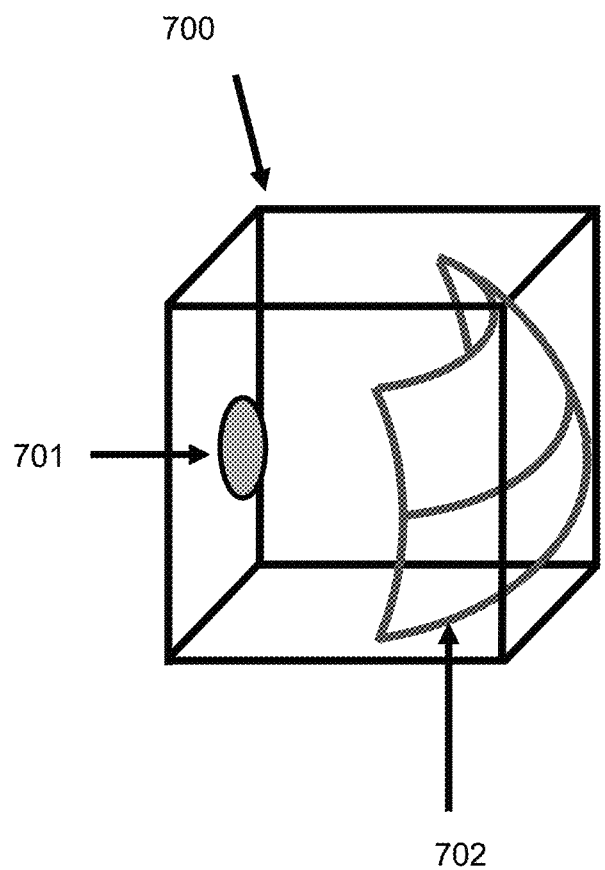
FIG. 7 illustrates the light painting imaging device (LPID).

FIG. 7 illustrates the light painting imaging device (LPID). 700 illustrates a camera box. 701 illustrates a converging lens, which is on a bi-axial rotatable mount. 702 illustrates the double curved detector array. Note that an aspect is a compact design is for the LPID designs with smaller focal lengths per FIG. 12.

Figure 8:
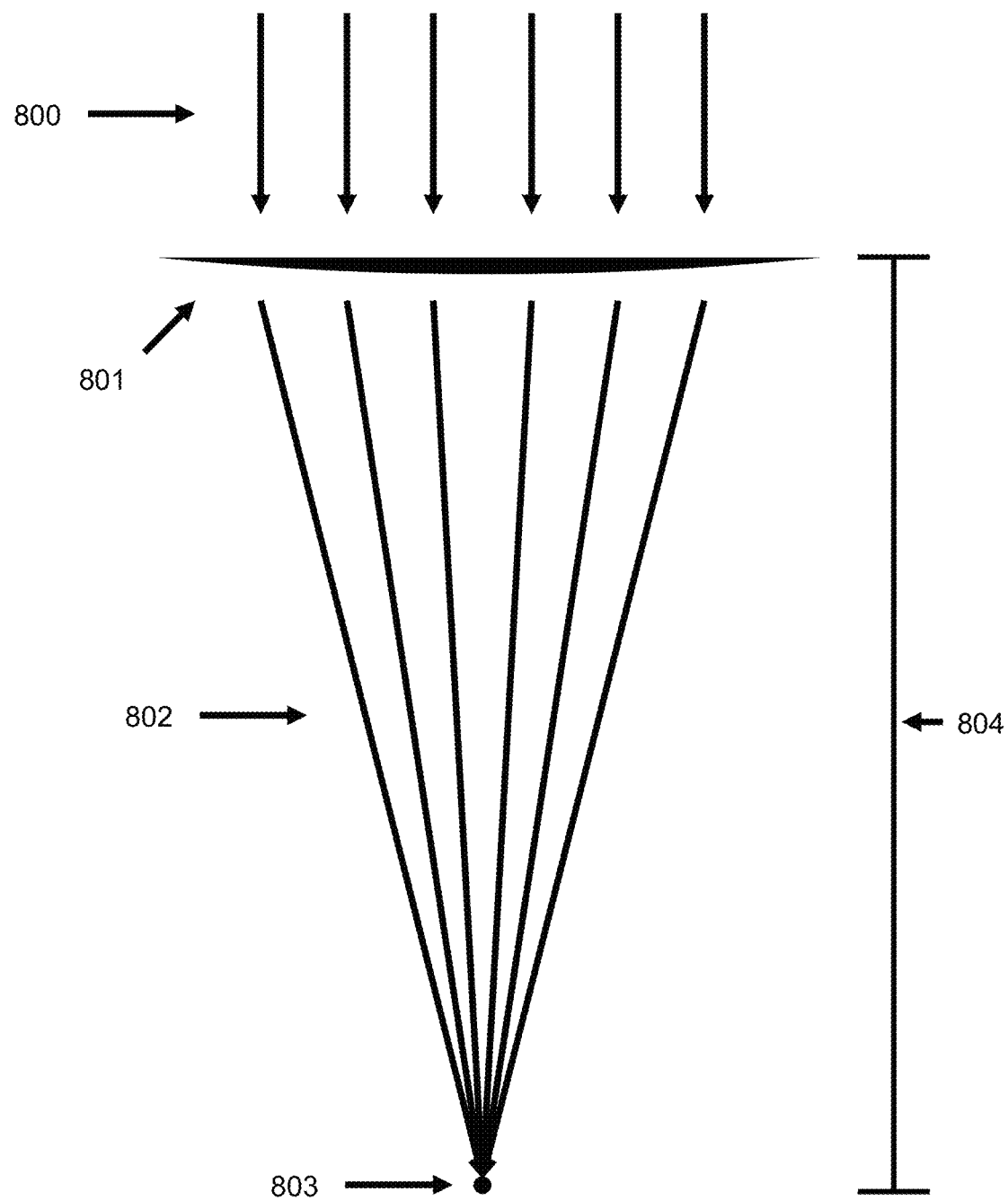
FIG. 8 illustrates optimization of the lens for the light painting imaging device.

FIG. 8 illustrates optimization of the lens for the light painting imaging device. 800 illustrates the incoming light from an environment. In this example, parallel or near parallel light is shown. 801 illustrates a lens. In the preferred embodiment, the lens is a narrow angle lens. Also, in the preferred embodiment, the lens is located on a rotatable mount. In the preferred embodiment, the diameter of the lens will be selected based on the desired application of the lens. For example, for very low light imaging, such as certain space objects, imaging will be optimized when using a large diameter lens including 12 inch diameter or more. For daytime imaging of bright objects, high quality imaging can be performed with a smaller diameter lens. In some embodiments, a Fresnel lens can be utilized. 802 illustrates wherein the light exiting the lens 801 is converging.

803 illustrates the focal point of the lens 801. 804 illustrates the focal length. The focal length, f is equal to R/2 wherein R is the radius of curvature of the lens's surface. A novel aspect of this invention is the ability to collect sufficient light from a tiny object way far in the distance to be measured. An aspect of this invention is to use a long focal length and a narrow angular field of view of the lens.

Figure 9:
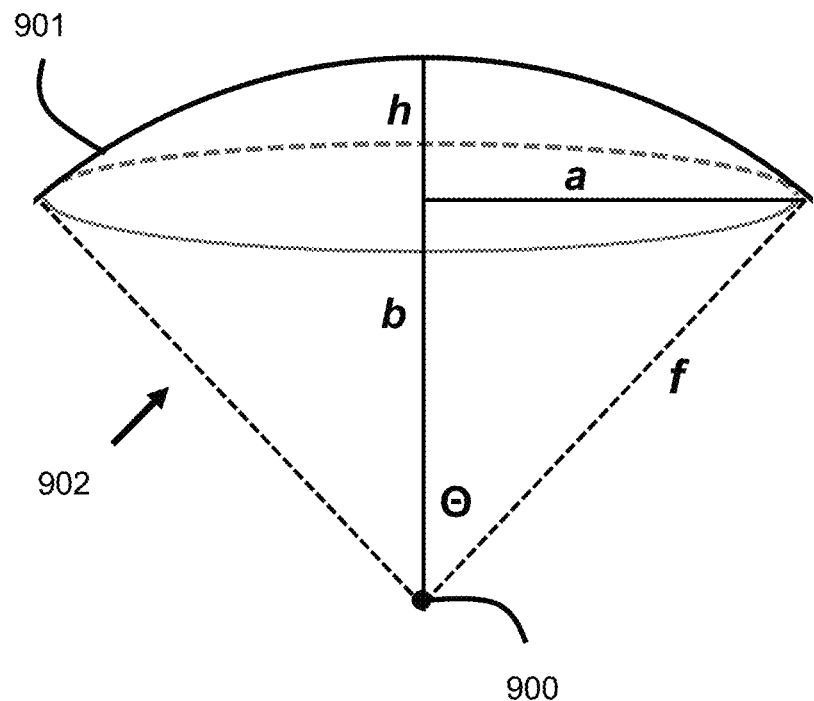
FIG. 9 illustrates selection of detector size for the light painting imaging device (LPID).

FIG. 9 illustrates selection of detector size for the light painting imaging device (LPID). In this example, the detector is a partial spherical shape. 900 illustrates the center of the lens. 901 illustrates the curvature of the detector, which has a curvature equivalent to a portion of a sphere wherein the radius of the sphere is equal to the focal length of the lens. 902 illustrates a cone-shaped structure, which illustrates the relationship between the focal length and the detector. As the lens pitches and yaws about its center, the focal point will move over different portions of the detector and will remain in proximity to the detector. In the preferred embodiment, in proximity means the focal point is on a single detector element. In some embodiments, in proximity means the focal point is within less than 4 detector elements. In some embodiments, in proximity means the focal point is within less than 50 detector elements. In some embodiments, in proximity means the focal point is within less than 1000 detector elements. In some embodiments, in proximity means the focal point is within less than 1,000,000 detector elements. f illustrates the focal length. $\Theta$ illustrates half of the angular width of the detector. As shown in FIG. 1, the focal length, f, is equal to b+h. As shown in FIG. 1, b is equal to $f*\cos(\Theta)$. As shown in FIG. 1, h is equal to f−b. h is equal to $f-f*\cos(\Theta)$. Thus, the surface area of the detector is equal to $2*pi*f*(f-f*\cos(\Theta))$. Note that this figure is not to scale.

FIG. 10A illustrates a front view of a light painting imaging device at a time point. 1000A illustrates a lens, which is in a first orientation. This first orientation corresponds to collecting light from a first direction from an environment. In the preferred embodiment, the lens is a converging lens. 1001A illustrates a cross-section of a detector from the front view. In the preferred embodiment, the detector is a double curved detector. In some embodiments, the double curved detector can be a portion of a sphere. In some embodiments, the double curved detector could be circular in shape if viewed from the position of the lens. In some embodiments, the double curved detector could be other shapes if viewed from the top. It should be noted that the detector is oriented and positioned such that elements on the detector are at the focal point of the lens. 1002A illustrates incoming light. Note that this light is coming from the first direction. In this example, the incoming light is from above, such as could be done from a telescope pointed up at the sky. Other orientations can also be performed to achieve a variety of tasks, such as from a satellite looking down at the earth, on an airplane, indoors, outdoors, underwater or even in space viewing features in far reaching distances. 1003A illustrates the light that passes through the lens 1000A and converges at the lens's focal point onto the detector at location 104A, which has an x-value of 400. 1005A illustrate the maximum "x-value". In this example, the maximum x-value is 500. 1006A illustrate the minimum "x-value". In this example, the minimum x-value is 1. Lens 1000A is in a first orientation and light from the first direction contacts a double curved detector at an x-value of 400. The y-value is illustrated in FIG. 10B.

FIG. 10B illustrates a side view of the light painting imaging device at the time point in FIG. 10A. 1000A illustrates the lens, which is in the first orientation. 1001B illustrates a cross-section of a detector from the side view. 1002A illustrates incoming light. Note that this light is coming from the first direction. 1003A illustrates the light that passes through the lens 1000A and converges at the lens's focal point onto the detector at location 1004B, which has an y-value of 400. 1005B illustrates the maximum "y-value". In this example, the maximum y-value is 500. 1006B illustrate the minimum "y-value". In this example, the minimum y-value is 1.

Lens 100A is in a first orientation and light from the first direction contacts a double curved detector at an y-value of 400. Thus, at this time point in FIG. 1A and FIG. 1B, the lens gathers light from a first direction and converges its light to (x,y) coordinate (400,400) on the detector array.

FIG. 10C illustrates a front view of the light painting imaging device at a subsequent time point. 1000B illustrates the lens, which is in the second orientation. The second orientation is different from the first orientation. This second orientation corresponds to collecting light from a second direction. The second direction is different from the first direction. 1001A illustrates a cross-section of the detector from the front view. 1002B illustrates incoming light. Note that this light is coming from the second direction. 1003B illustrates the light that passes through the lens 100B and converges at the lens's focal point onto the detector at location 1004C, which has an x-value of 450. 1005A illustrates the maximum "x-value". In this example, the maximum x-value is 500. 1006A illustrates the minimum "x-value". In this example, the minimum x-value is 1. Lens 1000B is in the second orientation and light from the second direction contacts the double curved detector at an x-value of 450.

FIG. 10D illustrates a side view of a light painting imaging device at the subsequent time point in FIG. 10C. 1000B illustrates the lens, which is in the second orientation. 1001B illustrates the cross-section of the detector from the side view. 1002B illustrates incoming light from the second direction. Note that the second direction is different from the first direction. 1003B illustrates the light that passes through the lens 1000B and converges at the lens's focal point onto the detector at location 1004D, which has an y-value of 400. 1005B illustrates the maximum "y-value". In this example, the maximum y-value is 500. 1006B illustrates the minimum "y-value". In this example, the minimum y-value is 1. Thus, at this subsequent time point in FIG. 1C and FIG. 1D, the lens gathers light from a second direction and converges its light to (x,y) coordinate (450,400) on the detector array. This novel design would allow more light concentrated on a single detector. In some embodiments, even if the precise pointing direction of the lens was not known, the image could still be precise because the gimble is aligned nicely with the detector and it moves smoothly.

FIG. 11A illustrates data collection from a light painting imaging device (LPID) without filters. A table is shown to illustrate data collected from the LIPD without filters. The first column illustrates row #1. Note that a detector array will include a set of rows and columns. The second column illustrates pointing angle. Note that a single pointing angle is illustrated. Note that two pointing angles (a horizontal pointing angle and a vertical pointing angle) can be used. The third column illustrates time point, frequency and amplitude. Rows 1, Detector 1 corresponds to a pointing angle of −0.499° and has (1, Frequency, Amplitude). Rows 1, Detector 2 corresponds to a pointing angle of −0.498° and has (2, Frequency, Amplitude). Rows 1, Detector 3 corresponds to a pointing angle of −0.497° and has (3, Frequency, Amplitude). Rows 1, Detector 500 corresponds to a pointing angle of 0° and has (500, Frequency, Amplitude). Rows 1, Detector 501 corresponds to a pointing angle of 0.001° and has (501, Frequency, Amplitude). Rows 1, Detector 998 corresponds to a pointing angle of 0.498° and has (998, Frequency, Amplitude). Rows 1, Detector 999 corresponds to a pointing angle of 0.499° and has (999, Frequency, Amplitude). Rows 1, Detector 1000 corresponds to a pointing angle of 0.500° and has (1000, Frequency, Amplitude).

FIG. 11B illustrates data collection from a light painting imaging device (LPID) with filters. Rows 1, Detector 1 corresponds to a pointing angle of −0.499° and has (R, Amplitude) collected at time point 1, (G, Amplitude) collected at time point 1001, and (B, Amplitude) collected at time point 2001. Note that "R" indicates a red filter, "G" indicates a green filter, and "B" indicates a blue filter. Note that in some embodiments, these filters can be positioned and re-positioned to allow sequential data acquisition. Rows 1, Detector 2 corresponds to a pointing angle of −0.498° and has (R, Amplitude) collected at time point 2, (G, Amplitude) collected at time point 1002, and (B, Amplitude) collected at time point 2002. Rows 1, Detector 3 corresponds to a pointing angle of −0.497° and has (R, Amplitude) collected at time point 3, (G, Amplitude) collected at time point 1003, and (B, Amplitude) collected at time point 2003. Rows 1, Detector 500 corresponds to a pointing angle of 0° and has (R, Amplitude) collected at time point 500, (G, Amplitude) collected at time point 1500, and (B, Amplitude) collected at time point 2500. Rows 1, Detector 501 corresponds to a pointing angle of 0.001° and has (R, Amplitude) collected at time point 501, (G, Amplitude) collected at time point 1501, and (B, Amplitude) collected at time point 2501. Rows 1, Detector 998 corresponds to a pointing angle of 0.498° and has (R, Amplitude) collected at time point 998, (G, Amplitude) collected at time point 1998, and (B, Amplitude) collected at time point 2998. Rows 1, Detector 999 corresponds to a pointing angle of 0.499° and has (R, Amplitude) collected at time point 999, (G, Amplitude) collected at time point 1999, and (B, Amplitude) collected at time point 2999. Rows 1, Detector 1000 corresponds to a pointing angle of 0.500° and has (R, Amplitude) collected at time point 1000, (G, Amplitude) collected at time point 2000, and (B, Amplitude) collected at time point 3000. A novel aspect of this patent is wherein every pixel for an image is collected at a different time point. A range of timing and scan patterns can be utilized in this system. In this example, for the first row, all data from red filter is collected followed by all data from the green filter followed by all data from the blue filter. This example continued would include moving to row #2 and then again collecting all data from red filter is collected followed by all data from the green filter followed by all data from the blue filter. Then moving to row #3 and so on. In other examples, all data from all rows can be collected from using the red filter. Once the entirety of the data from using the red filter is accomplished, then all data from using the green filter can be collected second. Then, third, all data from using the blue filter. In some embodiments, delay periods may be present at various intervals during this data collection.

FIG. 12 illustrates the light painting imaging device (LPID) performance characteristics. A few designs are provided. Other combinations are possible. The third row will be discussed in detail. The first design feature is the radius of curvature of the detector. In this example, the radius of curvature of the detector array is 0.2 meters. This corresponds to f in FIG. 9. In this example, assume that the total angular field of view (FOV) is 10° and assume that half of the FOV is 5°. Smaller and larger FOVs are also possible. In this example, the surface area of the detector in m$^2$ is calculated by))2*3.14*0.20(0.20−0.20*cos(5°)), which equals 0.00096 m$^2$.

A question at this juncture would be how big is 0.00096 m$^2$ compared to a standard size camera detector, such as the detector used in the Cannon 5D Mark iii. The Cannon 5D Mark iii camera detector size measures 3.6 cm×2.4 cm, so it has a surface area of 0.000864 m$^2$. The Cannon 5D Mark iii detector array has 5784×3861 detector elements, so it totals 22.3 megapixels (MP). The detector in this example on row 3 of this figure has 24.7 MP and is 1.11 times the size of the Cannon 5D Mark iii detector. In this example, the detector is the shape of a section of the surface of a sphere wherein the edges of the section would form a circle. Next, take $(0.00096/3.14)^{0.5}$ to yield a 0.017 m radius of the detector. In this example, the detector array will partial-spherical shape have a radius of 2731 detectors. Next, determine the number of pixels/m² by taking the number of MP in the detector (24.67) times 1,000,000 and dividing that by the surface area of the detector (0.017) to yield 25,810,185,185 detector element/m². Along a linear length of a meter, there would be 160,655 detector elements. Each detector element would be 0.00000622 m in size. Next, the angular resolution will be equal to $2*\tan^{-1}$(detector element size/(2*/). This yields $2*\tan^{-1}(0.00000622/(2*0.20)$ or 0.00003112° per detector element. Thus, a column of 32,131 detector elements per degree. Since the detector has a diameter of 5,462 detector elements, from one end of the detector to the other end of the detector would cover 0.17°. In some embodiments, the focal point lands on a cluster of detector elements, rather than a single detector element. In some embodiments, when the focal point lands on a cluster of detector elements (e.g., a 5×5 cluster of detector elements), a lower spatial resolution is performed. In some embodiments, image processing is performed to sharpen the image based on analysis of each detector element's signal in the cluster of detector elements. In the preferred embodiment, the curvature of the detector matches the focal length of the lens. In some embodiments, a mirror system is utilized wherein the mirror's curvature matches that of the detector. In some embodiments, a deformable detector is used wherein said deformable detector can form to multiple shapes. In some embodiments, a deformable lens is used wherein said deformable lens can form to multiple shapes. The preferred embodiment of this is a Fresnel lens wherein the groves are adjustable, movable in position or orientation so as to change the focal length. Some embodiments comprise a focal point of smaller than 0.01 meters. Some embodiments comprise a focal point of at least 0.01 meters. Some embodiments comprise a focal point of at least 0.05 meters. Some embodiments comprise a focal point of at least 0.20 meters. Some embodiments comprise a focal point of at least 0.50 meters. Some embodiments comprise a focal point of at least 1.00 meters. Some embodiments comprise a radius of curvature of the lens of smaller than 0.01 meters. Some embodiments comprise a radius of curvature of the lens of at least 0.01 meters. Some embodiments comprise a radius of curvature of the lens of at least 0.05 meters. Some embodiments comprise a radius of curvature of the lens of at least 0.20 meters. Some embodiments comprise a radius of curvature of the lens of at least 0.50 meters. Some embodiments comprise a radius of curvature of the lens of at least 1.00 meters.

FIG. 13A illustrates a light painting imaging device cluster at a time point. 1300A illustrates the location where light from the first LPID in the LIPD-C is focusing at the time point. 1301A illustrates the location where light from the second LPID in the LIPD-C is focusing at the time point. 1302A illustrates the location where light from the third LPID in the LIPD-C is focusing at the time point. 1303A illustrates the location where light from the fourth LPID in the LIPD-C is focusing at the time point.

FIG. 13B illustrates the light painting imaging device cluster at a subsequent time point. 1300B illustrates the location where light from the first LPID in the LIPD-C is focusing at the subsequent time point. 1301B illustrates the location where light from the second LPID in the LIPD-C is focusing at the subsequent time point. 1302B illustrates the location where light from the third LPID in the LIPD-C is focusing at the subsequent time point. 1303B illustrates the location where light from the fourth LPID in the LIPD-C is focusing at the subsequent time point. In this example, the first LPID, the second LPID, the third LPID and the fourth LPID are all collecting light from the same pointing angle. In some embodiments, the first LPID, the second LPID, the third LPID and the fourth LPID can collect light from the different pointing angle. For example, at a given time point, the first LPID can be performing imaging with a vertical angle of 0.001° and horizontal angle of 0.001° and the second LIPD can be performing imaging with a vertical angle of 1.001° and horizontal angle of 0.001°.

Figure 14:
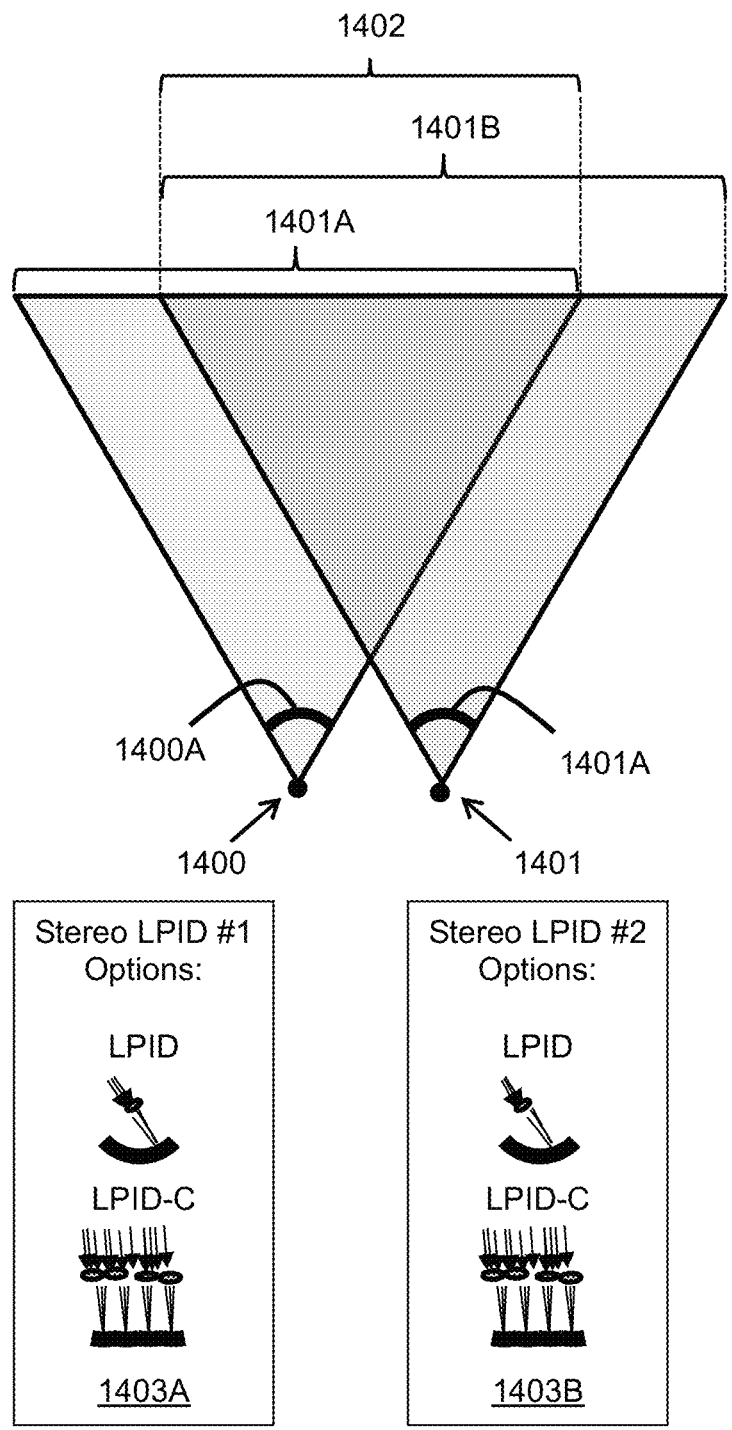
FIG. 14 illustrates a top-down view of a stereoscopic light painting imaging device (SLPID).

FIG. 14 illustrates a top-down view of a stereoscopic light painting imaging device (SLPID). 1400 illustrates a left stereoscopic camera. 1401 illustrates a right stereoscopic camera. 1400A illustrates the angular field of view for the left stereoscopic camera 1400. 1400B illustrates the angular field of view for the right stereoscopic camera 1401. 1401A illustrates a first field of regard for the left stereoscopic camera 1400. 1401B illustrates a second field of regard for the right stereoscopic camera 1401. 1402 illustrates the overlap from the first field of regard and the second field of regard. 1403A illustrates options for the first light painting imaging device (LPID) camera system, which corresponds to the first stereoscopic camera 100 and includes a single light painting imaging device (LPID) and a light painting imaging device cluster (LPID-C). 1403B illustrates options for the second light painting imaging device (LPID) camera system, which corresponds to the second stereoscopic camera and includes a single light painting imaging device (LPID) and a light painting imaging device cluster (LPID-C). Note that convergence of the left stereoscopic camera 100 and the right stereoscopic camera 101 can be implemented through techniques taught in U.S. Ser. No. 17/225,610, AN IMPROVED IMMERSIVE VIEWING EXPERIENCE, and U.S. patent application Ser. No. 17/237,152, AN IMPROVED IMMERSIVE VIEWING EXPERIENCE, which are incorporated by reference in their entirety. In some embodiments, stereoscopic imagery can be collected using two DARPA Argus cameras placed at a stereoscopic distance from each other, as shown in 103A and 103B.

Figure 15:
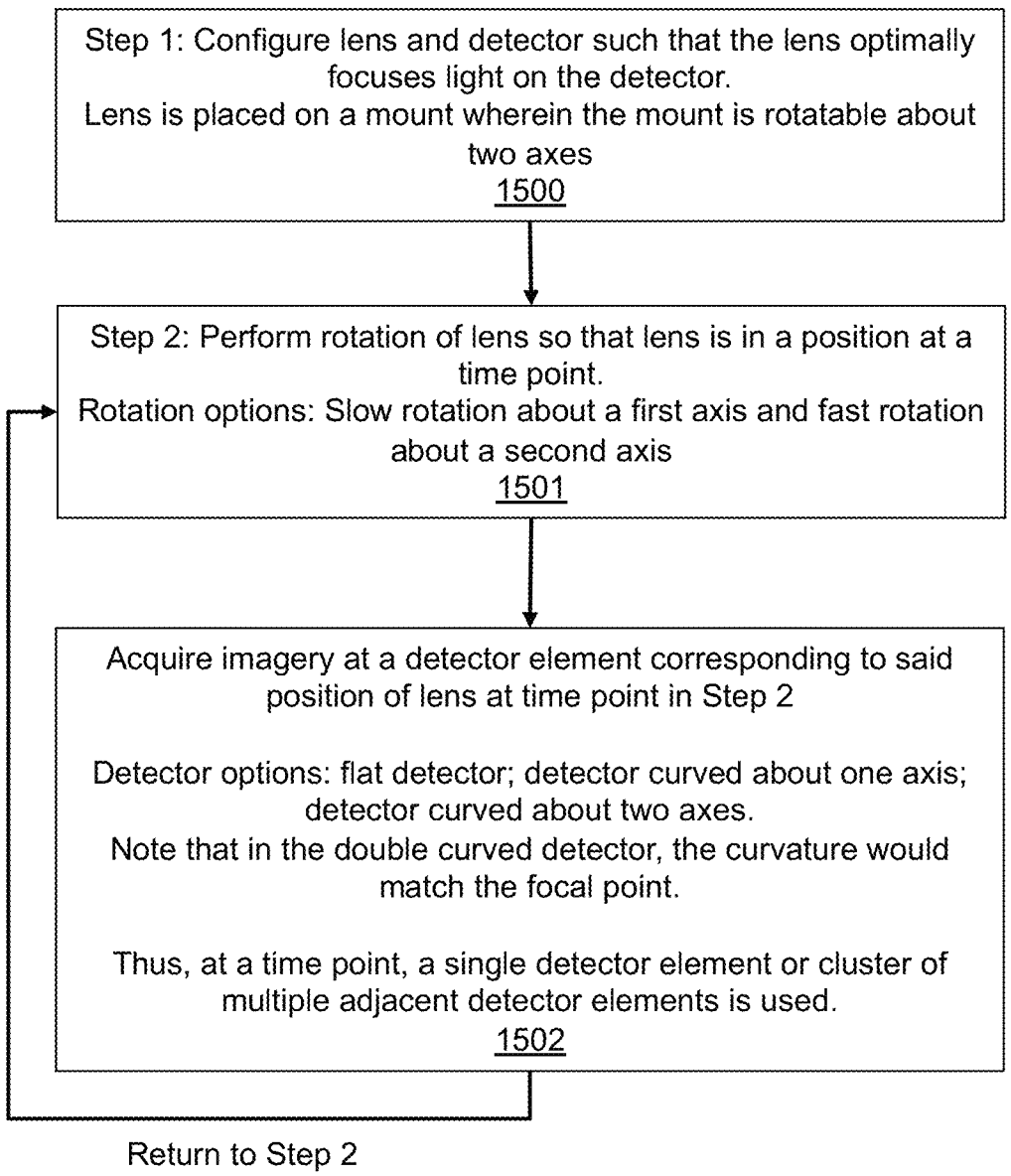
FIG. 15 illustrates a flow diagram for the two-axes rotatable converging lens.

FIG. 15 illustrates a flow diagram for the two-axes rotatable converging lens. 1500 illustrates Step 1, which is to configure lens and detector such that the lens optimally focuses light on the detector. The lens is placed on a mount wherein the mount is rotatable about two axes. 1501 illustrates Step 2, which is to perform rotation of lens so that lens is in a position at a time point. Rotation options: Slow rotation about a first axis and fast rotation about a second axis. 1502 illustrates acquiring imagery at a detector element corresponding to said position of lens at time point in Step 2. Detector options include: flat detector; detector curved about one axis; detector curved about two axes. Note that in the double curved detector, the curvature would match the focal point. Thus, at a time point, a single detector element or cluster of multiple adjacent detector elements is used.

Figure 16:
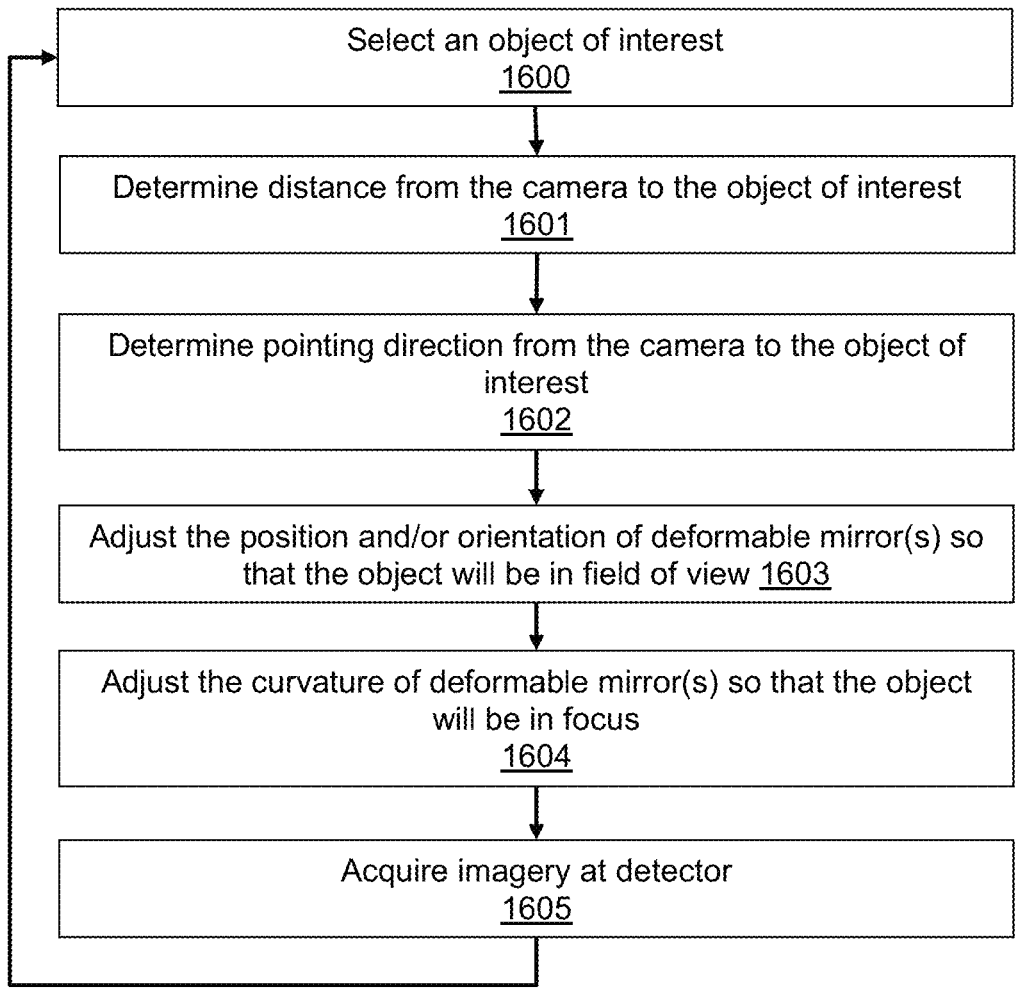
FIG. 16 illustrates object tracking using an adaptable mirror.

FIG. 16 illustrates object tracking using an adaptable mirror. 1600 illustrates selecting an object of interest. This can be performed using AI, ATR or eye tracking of a user. 1601 illustrates determining a distance from the camera to the object of interest. This can be accomplished using distance measuring devices, including LIDAR or LRF. 1602 illustrates determining a pointing direction from the camera to the object of interest. 1603 illustrates adjusting the position and/or orientation of deformable mirror(s) so that the object will be in field of view. 1604 illustrates adjust the curvature of deformable mirror(s) so that the object of interest will be in focus. In some embodiments, multiple fixed-shaped mirrors can be used in the system and these can be changed out to image the scene. 1605 illustrates acquiring imagery at detector. This can allow improved viewing, such as viewing of a butterfly at a long distance so that it can be seen with excellent stereoscopic imaging. Other things that can be viewed include a bird swooping down. This same process can be used with an adaptable lens.

FIG. 17A illustrates a deformable mirror yielding a first focal point at a first time point, t=N. 1700A illustrates a mirror with a first curvature. A supporting apparatus is used to deform the mirror to the first curvature. In the preferred embodiment, the first curvature is formed by a system of actuators 1701A. The first curvature yields a first focal point 1702A FIG. 17B illustrates a deformable mirror yielding a second focal point at a second time point, t=N+1. 1700B illustrates a mirror with a second curvature. A supporting apparatus is used to deform the mirror from the first curvature to the second curvature wherein the second curvature is different from the first curvature. In the preferred embodiment, the second curvature is formed by a system of actuators 1701B. Drivers may be used. The second curvature yields a second focal point 102B. Pneumatic compression can be used to deform the mirrors as well. In the preferred embodiment, the curvature is formed to cause the focal point of the deformable mirror to be at a specific distance wherein the specific distance is the distance from the mirror to an object of interest. For example, consider a man going hunting for a boar at night from a tower. The amount of light in the scene is very dim. The man is trying to closely survey the object in the bushes at a distance away. The method comprises using a laser range finder (or LIDAR) to determine the precise distance from the deformable mirror to the object of interest. The object of interest is determined to be 70 feet away. The deformable mirror forms a curvature such that the focal point is at 70 feet away. In some embodiments, the deformable mirror is pointed towards the object of interest. In some embodiments, the deformable mirror forms a shape to control the distance of the focal point and the direction of the focal point. The apex of the curvature can be located towards the top of the mirror to cause the focal point to shift downwards. The apex of the curvature can be located towards the bottom of the mirror to cause the focal point to shift upwards. The apex of the curvature can be located towards the right of the mirror to cause the focal point to shift to the left. The apex of the curvature can be located towards the left of the mirror to cause the focal point to shift to the right. The apex of the curvature can shift at various locations along the mirror so as to control the location of the focal point. In some embodiments, two adjustable mirrors can be utilized. The first adjustable mirror can be located at a stereo distance from the second adjustable mirror. The imagery from the first adjustable mirror can be presented on a left eye display and the imagery from the second adjustable mirror can be presented on a right eye display to yield stereoscopic imagery for a user wearing a head display unit with a left eye display and a right eye display. In some embodiments, eye tracking of a user is performed to determine wherein the scene a user is looking. Then the deformable mirror(s) can adjust the curvatures to optimize imaging of the location where a user is looking within the scene. Additional combinable features are taught in U.S. Ser. No. 16/997,830, ADVANCED HEAD DISPLAY UNIT FOR FIRE FIGHTERS, which is incorporated by reference in its entirety. In some embodiments, the focal point of the first adjustable mirror for the left eye display and the focal point of the second adjustable mirror for the right eye display are superimposed to allow imagery with a convergence point. In some embodiments, the focal point of the first adjustable mirror for the left eye display and the focal point of the second adjustable mirror for the right eye display are not superimposed to allow stereoscopic imagery without a convergence point. This can be used for looking straight off in the distance over long distances. In some embodiments, the deformable mirror can adjust for wavefront correction.

Figure 18:
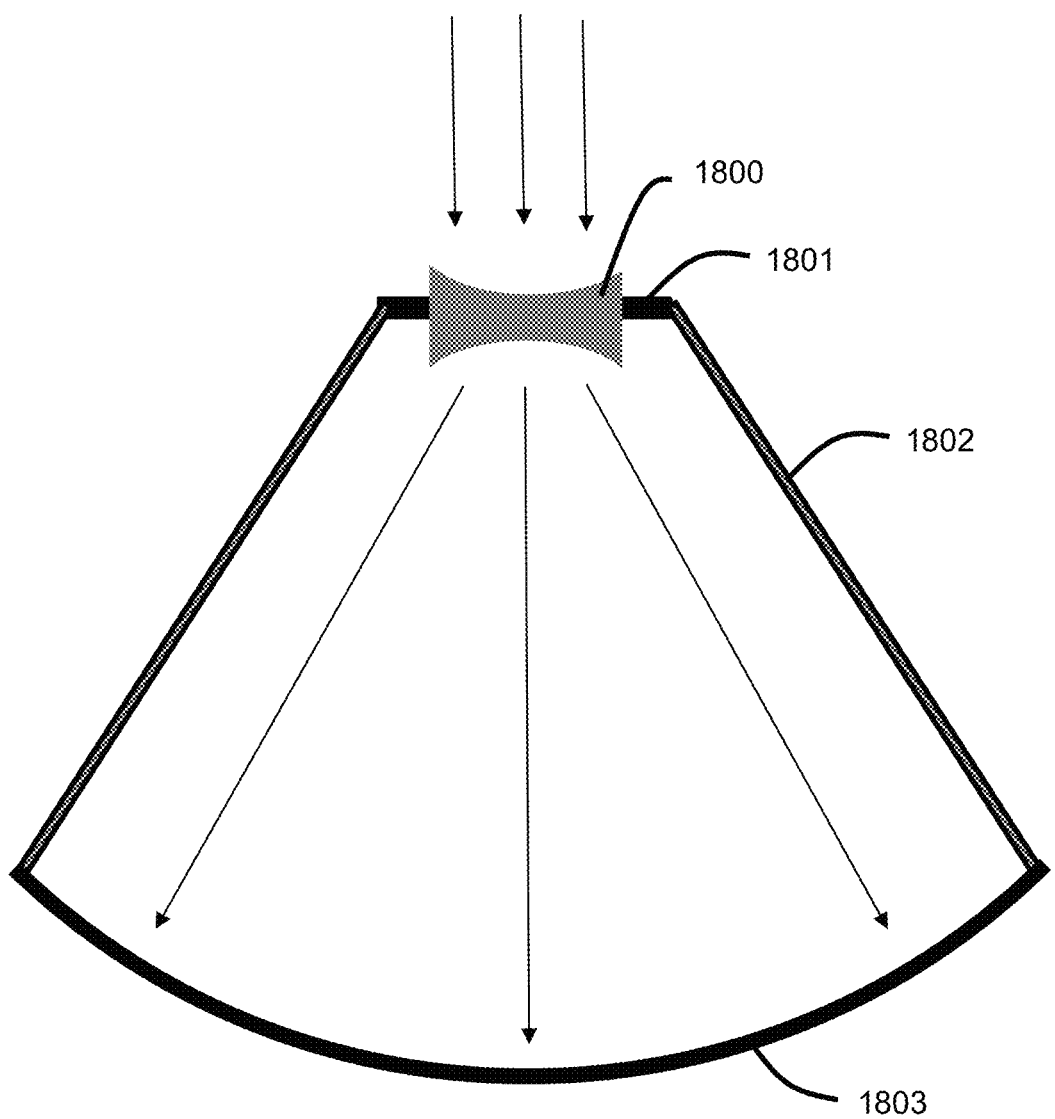
FIG. 18 illustrates a diverging lens with a double curved detector.

FIG. 18 illustrates the light painting imaging device. 1800 illustrates a diverging lens. Converging lenses are also possible. 1801 illustrates a mount for the diverging lens 1800. 1802 illustrates housing for blocking ambient light. This can be made of opaque material. 1803 illustrates a detector wherein the detector is shaped as a partial spherical shape. This is useful because it is able to correct for pincushion distortion and barrel distortion.

Figure 19:
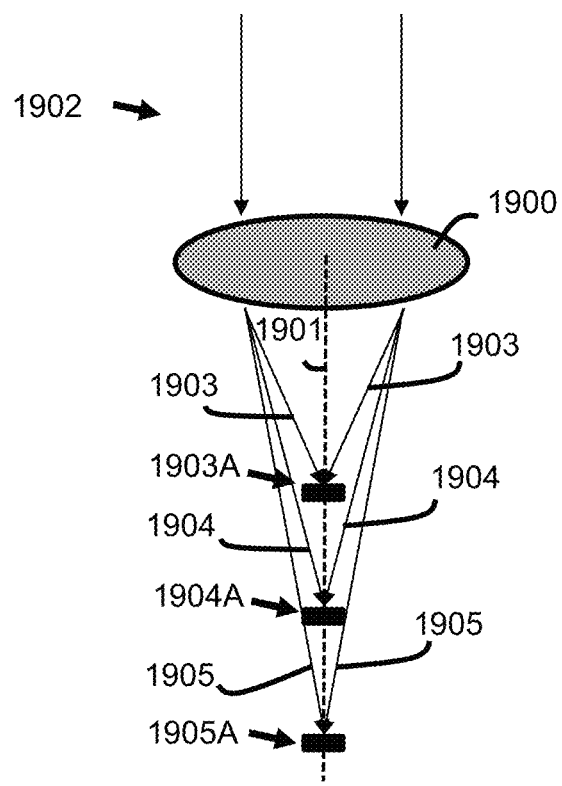
FIG. 19 illustrates a stacked layout for detectors.

FIG. 19 illustrates a stacked layout for detectors. 1900 illustrates a converging lens. 1901 illustrates the principal axis of the converging lens 1900. 1902 illustrates light from an environment passing into the lens 1900. In this example, the light is made of multiple frequencies. 1903 illustrates a first frequency of light, which refracts to a first focal point. 1903A illustrates a first detector located at the first focal point. 1904 illustrates a second frequency of light, which refracts to a second focal point. 1904A illustrates a second detector located at the second focal point. 1905 illustrates a third frequency of light, which refracts to a third focal point. 1905A illustrates a third detector located at the third focal point. Note that this stacked layout can include at least two detectors. Each detector can be located on the principal axis of the lens. In the preferred embodiment, the first detector 1903A is for blue light, the second detector 1904A is for green light and the third detector 1905A is for red light.

FIG. 20A illustrates the adaptable mirror concept. 2000A illustrates light from an external environment. 2001A illustrates an adaptable mirror. The adaptable mirror is one that deforms to optimize imaging of an object of interest in the scene. For example, assume there is a brick laying on top of a wall at 300 feet away. The mirror can be adaptable so as to deform to yield a focal point at 300 feet. The mirror can also achieve a pointing affect either by deforming to yield a specific shape of the mirror or by being placed on a rotatable mount so as to yield the pointing direction towards the object of interest. In some embodiments, the object of interest can be determined by an artificial intelligence algorithm. In some embodiments, the object of interest can be determined by an automatic target recognition (ATR) system. In some embodiments, the object of interest can be determined by an eye tracking system of a user, as is taught in U.S. Ser. No. 16/997,830, ADVANCED HEAD DISPLAY UNIT FOR FIRE FIGHTERS, which is incorporated by reference in its entirety. 2002A illustrates a detector array (or sensor). The sensor can be planar or non-planar so as to optimize imagery received from the adaptable mirror 2001A. In some embodiments, additional mirror(s), lens(es), shutter(s), rotatable mount(s), aperture(s) can also be integrated into the adaptable mirror system. In some embodiments, an eye piece can be used in place of the detector 2002A. In some embodiments, image stabilization is also performed. A gyroscope or gimbal can be used.

FIG. 20B illustrates the adaptable lens concept. 2000B illustrates light from an external environment. 2001B illustrates an adaptable lens. The adaptable lens is one that deforms to optimize imaging of an object of interest in the scene. For example, assume there is a brick laying on top of a wall at 300 feet away. The lens can be deform so as to deform to yield a focal point at 300 feet. This can be constructed by using material that is flexible. Alternatively, a Fresnel lens can be used wherein the angles of the grooves in the lens can change. The adaptable lens can also achieve a pointing affect by being placed on a rotatable mount so as to yield the pointing direction towards the object of interest. In some embodiments, the object of interest can be determined by an artificial intelligence algorithm. In some embodiments, the object of interest can be determined by an automatic target recognition (ATR) system. In some embodiments, the object of interest can be determined by an eye tracking system of a user, as is taught in U.S. Ser. No. 16/997,830, ADVANCED HEAD DISPLAY UNIT FOR FIRE FIGHTERS, which is incorporated by reference in its entirety. 2002B illustrates a detector array (or sensor). The sensor can be planar or non-planar so as to optimize imagery received from the adaptable mirror 2001B. In some embodiments, additional mirror(s), lens(es), shutter(s), rotatable mount(s), aperture(s) can also be integrated into the adaptable mirror system. In some embodiments, an eye piece can be used in place of the detector 2002B. In some embodiments, image stabilization is also performed.

FIG. 20C illustrates a camera design with stereoscopic adaptable mirrors. 2000C illustrates light from an external environment. 2001C illustrates a left-sided adaptable mirror, which reflects light from the external environment onto the left detector 2002C. 2001D illustrates a right-sided adaptable mirror, which reflects light from the external environment onto the right detector 2002D. The imagery from the left detector 102C is presented on the left eye display of a head display unit (HDU). The imagery from the right detector 2002D is presented on the right eye display of the HDU. A user wearing the HDU sees the left eye imagery on the left eye display and right eye imagery on the right eye display, so had stereoscopic depth perception with great detail of the object of interest. In some embodiments, stereoscopic image stabilization is also performed. Some embodiments use a focal point from a left curved mirror and the same focal point for a right curved mirror. Together, these will optimize imagery of a specific spot in 3D space.

FIG. 20D illustrates a camera design with stereoscopic adaptable lenses. 2000D illustrates light from an external environment. 2001E illustrates a left-sided adaptable lens, which refracts light from the external environment onto the left detector 2002E. 2001F illustrates a right-sided adaptable lens, which refracts light from the external environment onto the right detector 2002F. The imagery from the left detector 2002E is presented on the left eye display of a HDU. The imagery from the right detector 2002F is presented on the right eye display of the HDU. A user wearing the HDU sees the left eye imagery on the left eye display and right eye imagery on the right eye display, so had stereoscopic depth perception with great detail of the object of interest. In some embodiments, stereoscopic image stabilization is also performed. Some embodiments use stereo distance based on a distance chart.

FIG. 21A illustrates head display unit lens positions at time=L. 2100A illustrates a top-down view of the head display unit. 2101A illustrates a lens for the left eye display, which a user will look through.

2102A illustrates a lens for the right eye display, which a user will look through.

FIG. 21B illustrates head display unit lens positions at time=L+1. 2100B illustrates the top-down view of the head display unit. 2101B illustrates the lens for the left eye display, which a user will look through.

2102B illustrates the lens for the right eye display, which a user will look through. Note that the lens for the left eye display 2101B and the lens for the right eye display 2102B have now been shifted so that they are closer together. This can be performed through motorized control of the lenses, which can adapt to a user's face. An eye tracking system can be implemented to allow optimized lens placement for a user in real time. Thus, the lenses can move closer to each other or farther away from each other.

FIG. 21C illustrates head display unit lens positions at time=M. 2100C illustrates a view looking into a head display unit. 2101C illustrates a lens for the left eye display, which a user will look through. 2102C illustrates a lens for the right eye display, which a user will look through.

FIG. 21D illustrates head display unit lens positions at time=M+1. 2100D illustrates a view looking into the head display unit. 2101D illustrates a lens for the left eye display, which a user will look through. 2102D illustrates a lens for the right eye display, which a user will look through. Note that the lens for the left eye display 2101D and the lens for the right eye display 2102D have now been shifted so that they are located higher up on the head display unit. Also, note that the position of the lens for the right eye display is ever so slightly higher than the left. In some embodiments, the lens for the left eye display and the lens for the right eye display can shift independently from one another. In some embodiments, the display for the left eye and the display for the right eye can also shift in position or change in orientation in accordance with eye tracking. This can be performed through motorized control of the lenses, which can adapt to a user's face. An eye tracking system can be implemented to allow optimized lens placement for a user in real time. Thus, the lens for the left eye can move up, down, left or right. Additionally, the lens for the right eye can move up, down, left or right.

FIG. 21E illustrates head display unit lens orientations at time=N. 2100E illustrates a top-down view of a left portion of a head display unit. 2101E illustrates a lens for the left eye display, which a user will look through. 2102E illustrates a lens for the right eye display, which a user will look through. 2103E illustrates a top-down view of a right portion of a head display unit. Note that the left portion of the head display unit 100E and the right portion of the head display unit 103E are in line with one another.

FIG. 21F illustrates head display unit lens orientations at time=N+1. 2100F illustrates a top-down view of a left portion of a head display unit. 2101F illustrates a lens for the left eye display, which a user will look through. 102F illustrates a lens for the right eye display, which a user will look through. 2103F illustrates a top-down view of a right portion of a head display unit. Note that the left portion of the head display unit 2100F and the right portion of the head display unit 103F are canted with respect to one another. This is performed to account for convergence of a user. An eye tracking system is implemented and when convergence of the user is determined, the head display unit changes its configuration to adjust for a user's convergence. This can be performed through motorized control of the lenses, which can adapt to a user's face. An eye tracking system can be implemented to allow optimized lens placement for a user in real time. Thus, the left portion of the head display unit can move up, down, left or right. Additionally, the right portion of the head display unit can move up, down, left or right.

Throughout the entirety of the present disclosure, use of the articles "a" or "an" to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. The device(s) or computer systems that integrate with the processor(s) may include, for example, a personal computer(s), workstation(s) (e.g., Sun, HP), personal digital assistant(s) (PDA(s)), handheld device(s) such as cellular telephone(s), laptop(s), handheld computer(s), or another device(s) capable of being integrated with a processor(s) that may operate as provided herein. Accordingly, the devices provided herein are not exhaustive and are provided for illustration and not limitation. References to "a microprocessor and "a processor, or "the microprocessor and "the processor." may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor or "processor terminology may thus also be understood to include a central processing unit, an arithmetic logic unit, an application-specific integrated circuit (IC), and/or a task engine, with such examples provided for illustration and not limitation. Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where Such memory may be contiguous and/or partitioned based on the application. Accordingly, references to a database may be understood to include one or more memory associations, where such references may include commercially available database products (e.g., SQL, Informix, Oracle) and also include proprietary databases, and may also include other structures for associating memory Such as links, queues, graphs, trees, with such structures provided for illustration and not limitation. References to a network, unless provided otherwise, may include one or more intranets and/or the Internet, as well as a virtual network. References hereinto microprocessor instructions or microprocessor-executable instructions, in accordance with the above, may be understood to include programmable hardware.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems. Throughout the entirety of the present disclosure, use of the articles "a" or "an" to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art. Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method comprising:
 using a converging lens to refract light from an environment
 wherein said converging lens has a focal point,
 wherein said converging lens focuses said light from said environment directly onto a detector array,
 wherein said detector array comprises a curvature such that all points on said detector array are equidistant from a center of said lens; and
 wherein a distance from a point on said detector array to said center of said lens is equal to said lens's focal length,
 rotating said converging lens about a first axis to adjust the yaw and about a second axis to adjust the pitch to cause said focal point to move over said detector array;
 recording data from said detector array, and
 using said light received at said detector array to generate an image of said environment.

2. The method of claim 1 further comprising:
 wherein said converging lens is located on a rotatable mount;
 wherein said rotatable mount is configured to rotate said converging lens about a first axis;
 wherein said rotatable mount is configured to rotate said converging lens about a second axis;
 wherein said first axis is perpendicular to a principal axis of said converging lens;
 wherein said second axis is perpendicular to said principal axis of said converging lens;
 wherein said first axis and said second axis are perpendicular; and
 wherein said first axis, said second axis and said principal axis pass through a center of said converging lens.

3. The method of claim 2 further comprising:
 wherein said converging lens rotates about said first axis at a first rate;
 wherein said converging lens rotates about said second axis at a second rate; and wherein said first rate is at least 20 times faster than said second rate.

4. The method of claim 3 further comprising:
wherein said focal point moves over said detector array in a snake-like pattern wherein said snake-like pattern comprises:
moving across a first row of said detector array's from a first side to a second side; and
moving across a second row of said detector array from said second side to said first side wherein said second row and said first row are adjacent rows.

5. The method of claim 1 further comprising: wherein each detector element's position corresponds to a direction in said external environment.

6. The method of claim 1 further comprising:
for a time point, determining a pointing direction of said lens wherein said pointing direction of said lens corresponds to said principal axis of said lens; and
for said time point, determining at least one detector element in line with said pointing direction of said lens.

7. The method of claim 6 further comprising:
for said time point, recording data only from said at least one detector element.

8. The method of claim 6 further comprising:
wherein a rotation of said converging lens causes said pointing angle to change over time.

9. The method of claim 8 further comprising:
wherein from said converging lens and said detector array are parts of a camera system;
wherein said camera system has a field of view (FOV) of said environment;
wherein at a first time point said lens refracts light from a first pointing angle to a first location on said detector array;
wherein at a second time point said lens refracts light from a second pointing angle to a second location on said detector array;
wherein said second time point occurs after said first time point; and
wherein said second location is different from said first location.

10. The method of claim 9 further comprising wherein said detector array has a surface area of at least 0.00024 $m^2$.

11. The method of claim 1 further comprising wherein said lens has a radius of curvature of at least 0.05 meters.

12. The method of claim 1 further comprising determining colors of said light from said environment by using filters or by using a stacked layout for detectors.

13. The method of claim 1 further comprising:
wherein said detector array is non-planar; and
wherein a principal axis of said converging lens is oriented perpendicular to said detector array.

14. The method of claim 1 further comprising wherein said light from said environment is parallel or near parallel.

15. The method of claim 1 further comprising:
wherein from said converging lens and said detector array are parts of a camera system.

16. The method of claim 1 further comprising placing a cover wherein said cover is configured to:
allow light from said external environment, which passes through said converging lens, to reach said detector; and
block light from said external environment, which does not pass through said converging lens, to reach said detector.

17. An apparatus comprising:
a detector array; and
a converging lens wherein said converging lens refracts light directly from an environment,
wherein said converging lens has a focal point,
wherein said converging lens focuses said light from said environment onto said detector array,
wherein said detector array comprises a curvature such that all points on said detector array are equidistant from a center of said lens; and
wherein a distance from a point on said detector array to said center of said lens is equal to said lens's focal length,
rotating said converging lens about a first axis to adjust the yaw and about a second axis to adjust the pitch to cause said focal point to move over said detector array;
recording data from said detector array, and
using said light received at said detector array to generate an image of said environment.

18. An apparatus comprising:
a display wherein said display is configured to display an image,
wherein said image is obtained using a converging lens to refract light from an environment,
wherein said converging lens has a focal point,
wherein said converging lens focuses said light from said environment directly onto a detector array,
wherein said detector array comprises a curvature such that all points on said detector array are equidistant from a center of said lens; and
wherein a distance from a point on said detector array to said center of said lens is equal to said lens's focal length,
rotating said converging lens about a first axis to adjust the yaw and about a second axis to adjust the pitch to cause said focal point to move over said detector array;
recording data from said detector array, and
using said light received at said detector array to generate the image of said environment.

\* \* \* \* \*